(12) United States Patent
Baseuny

(10) Patent No.: US 11,285,196 B2
(45) Date of Patent: Mar. 29, 2022

(54) MULTIVALENT BIOLOGIC CONSTRUCTS FOR INDUCING A THERAPEUTIC MODULATION OF CELLULAR RESPONSE AND USES THEREOF

(71) Applicant: Eslam Abbas Baseuny, Asyut (EG)

(72) Inventor: Eslam Abbas Baseuny, Asyut (EG)

( * ) Notice: Subject to any disclaimer, the term of this patent is extended or adjusted under 35 U.S.C. 154(b) by 436 days.

(21) Appl. No.: 15/919,239

(22) Filed: Mar. 13, 2018

(65) Prior Publication Data

US 2019/0160161 A1    May 30, 2019

Related U.S. Application Data

(60) Provisional application No. 62/470,369, filed on Mar. 13, 2017.

(51) Int. Cl.
*A61K 39/02* (2006.01)
*A61P 17/00* (2006.01)
(Continued)

(52) U.S. Cl.
CPC .......... *A61K 39/02* (2013.01); *A61K 39/0005* (2013.01); *A61P 9/00* (2018.01); *A61P 17/00* (2018.01); *A61P 19/00* (2018.01); *A61K 2039/5154* (2013.01); *A61K 2039/5158* (2013.01); *A61K 2039/55555* (2013.01); *A61K 2039/57* (2013.01); *A61K 2039/625* (2013.01); *A61K 2039/70* (2013.01)

(58) Field of Classification Search
CPC ........ A61K 38/00; A61K 39/00; A61K 47/00; A61K 47/6929; A61K 47/6931; A61K 49/0093

USPC .............................. 424/9.1, 9.2, 184.1, 278.1
See application file for complete search history.

(56) References Cited

U.S. PATENT DOCUMENTS 5,453,490 A    9/1995 Hageman et al.
6,001,365 A    12/1999 Peterson et al.
(Continued)

FOREIGN PATENT DOCUMENTS

WO    WO96/39095    *  6/1996    ............... A61F 2/00

OTHER PUBLICATIONS

Rezwan et al. (Biomaterials, 27:3413-3431, 2006).*
(Continued)

*Primary Examiner* — Jana A Hines

(57) ABSTRACT

The presently-disclosed subject matter includes a multivalent biological construct that comprises a scaffold of anisometric dimensions, comprises a biodegradable hydrophobic core coated with a hydrophilic coat of fluidic material, and pluralities of bioactive molecules tethered to said scaffold. The multivalent biologic construct interacts simultaneously with multiple corresponding binding sites, increasing the functional affinity to induce an augmented therapeutic action in the form of stimulation, activation, competitive inhibition, consumptive inhibition or modulation of a biological system. Embodiments of the presently-disclosed subject matter include methods for preparation of the present construct as well as methods for using the present constructs to overcome cellular resistance, as thrombolytics, as competitive inhibitors, as consumptive inhibitors, as vaccines and as immunomodulators to treat a subject in need thereof.

9 Claims, 31 Drawing Sheets

(51) Int. Cl.
*A61K 39/00* (2006.01)
*A61P 19/00* (2006.01)
*A61P 9/00* (2006.01)

(56) References Cited

U.S. PATENT DOCUMENTS

| | | |
|---|---|---|
| 6,355,479 B1 | 3/2002 | Webb et al. |
| 8,629,098 B2 | 1/2014 | Fahmy et al. |
| 2012/0034155 A1 | 2/2012 | Hyde et al. |
| 2014/0370099 A1 | 12/2014 | Green et al. |
| 2016/0051698 A1 | 2/2016 | Schneck et al. |

OTHER PUBLICATIONS

Van der Weijden, Joep, Leonie E. Paulis, Martijn Verdoes, Jan CM van Hest, and Carl G. Figdor. "The right touch design of artificial antigen-presenting cells to stimulate the immune system." Chemical Science 5, No. 9 (2014): 3355-3367.

Knop, Katrin, Richard Hoogenboom, Dagmar Fischer, and Ulrich S. Schubert. "Poly (ethylene glycol) in drug delivery: pros and cons as well as potential alternatives." Angewandte chemie international edition 49, No. 36 (2010) 6288-6308.

Garboczi, David N., Deborah T. Hung, and Don C. Wiley. "HLA-A2-peptide complexes: refolding and crystallization of molecules expressed in *Escherichia coli* and complexed with single antigenic peptides." Proceedings of the National Academy of Sciences 89, No. 8 (1992): 3429-3433.

Rodenko, Boris, Mireille Toebes, Sine Reker Hadrup, Wim JE Van Esch, Annemieke M. Molenaar, Ton NM Schumacher, and Huib Ovaa. "Generation of peptide—MHC class I complexes through UV-mediated ligand exchange." Nature protocols 1, No. 3 (2006): 1120.

Vollers, Sabrina S., and Lawrence J Stm. "Class II major histocompatibility complex tetramer staining: progress, problems, and prospects." Immunology 123, No. 3 (2008): 305-313.

Stern, Lawrence J., and Don C. Wiley. "The human class II MHC protein HLA-DR1 assembles as empty αβ heterodimers in the absence of antigenic peptide." Cell 68, No. 3 (1992): 465-477.

Sloan, Victor S., Patricia Cameron, Gene Porter, Maureen Gammon, Miguel Amaya, Elizabeth Mellins, and Dennis M. Zaller. "Mediation by HLA-DM of dissociation of peptides from HLA-DR." Nature 375, No. 6534 (1995): 802.

Boulter, Jonathan M., Meir Glick, Penio T. Todorov, Emma Baston, Malkit Sami, Pierre Rizkallah, and Bent K. Jakobsen. "Stable, soluble T-cell receptor molecules for crystallization and therapeutics." Protein engineering 16, No. 9 (2003): 707-711.

Tang, Wei, Zi-Yong Sun, Ralph Pannell, Victor Gurewich, and Jian-Ning Liu. "An efficient system for production of recombinant urokinase-type plasminogen activator." Protein expression and purification 11, No. 3 (1997): 279-283.

Fairhead, Michael, and Mark Howarth. "Site-specific biotinylation of purified proteins using BirA." In Site-Specific Protein Labeling, pp. 171-184. Humana Press, New York, NY, 2015.

Alon, Ronen, Edward A. Bayer, and Meir Wilchek. "Streptavidin contains an RYD sequence which mimics the RGD receptor domain of fibronectin." Biochemical and biophysical research communications 170, No. 3 (1990): 1236-1241.

Nielson, Henrik. "RNA—Methods and Protocols." Humana Press, 2011.

Henrick, Bethany M., Xiao-Dan Yao, Kenneth Lee Rosenthal, and INFANT Study Team. "HIV-1 structural proteins serve as PAMPs for TLR2 heterodimers significantly increasing infection and innate immune activation." Frontiers in immunology 6 (2015): 426.

Abbas, Eslam. "Mathematical Analysis of the Probability of Spontaneous Mutations in HIV-1 Genome and Their Role in the Emergence of Resistance to Anti-Retroviral Therapy." arXiv preprint arXiv:1705.06132 (2017).

* cited by examiner

MULTIVALENT BIOLOGIC CONSTRUCTS FOR INDUCING A THERAPEUTIC MODULATION OF CELLULAR RESPONSE AND USES THEREOF

CROSS-REFERENCE TO RELATED APPLICATIONS

This application claims the benefit of the Provisional Patent Applications No. U.S. 62/470,369 filed on 13 Mar. 2017 by the present inventor.

STATEMENT REGARDING FEDERALLY SPONSORED RESEARCH OR DEVELOPMENT

Not Applicable.

REFERENCE TO SEQUENCE LISTING, A TABLE, OR A COMPUTER PROGRAM LISTING COMPACT DISC APPENDIX

Not Applicable.

DESCRIPTION

Field of Invention

The presently-disclosed subject matter relates to a multivalent biologic construct comprising multiple bioactive molecules tethered to a scaffold, methods of preparation of said construct, and methods for using said construct.

Background of the Invention

Augmenting the functional affinity of biologics to their target binding sites will help overcome cellular resistance and/or potentiate the effectiveness of such therapies. Multivalent biologic constructs with high functional affinity would achieve said goals via producing potent agonist that magnifying signal transduction or can be used as more effective antagonists to halt a signaling pathway. Additionally; manipulation and complexing of the composite of said multivalents can yield effective subunit vaccines and safer thrombolytics. Monomeric forms of protein ligands are unstable and have a low affinity to their corresponding receptors. Also; mimicking a signaling pathway, especially in the immune system, may also require simultaneous multiple ligand/receptor interactions to achieve the desired response. So the preparation of more effective multivalent biologics, with higher functional affinity and prolonged circulatory time, would help repress the burden of many diseases and reduce the resulting morbidity and mortality.

SUMMARY OF THE INVENTION

This summary describes several embodiments of the presently-disclosed subject matter, and in many cases, lists variations and permutations of these embodiments. This summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently-disclosed subject matter, whether listed in this summary or not. To avoid excessive repetition, this summary does not list or suggest all possible combinations of features.

The present invention is a multimeric biological construct, wherein several embodiments of said construct are used to treat a recipient in need thereof. The structure of the proposed multivalent biologic construct; comprises a scaffold of anisometric dimensions, which further comprises a biodegradable core coated with a hydrophilic coat of fluidic material, and a plurality of bioactive molecules tethered to said scaffold. Said scaffold can be a micro- or nano-granule, a micro- or nano-corpuscle, or streptavidin in one embodiment. Said granule comprises a non-spherical anisometric hydrophobic polymeric core of biocompatible, biodegradable substance, coated with a hydrophilic coat of fluidic material in which bioactive biomolecules are tethered via spacers.

Whereas; said corpuscle comprises an internal biocompatible liquid core contained within a thin, flexible, pliant biodegradable hydrophobic membrane, coated with a hydrophilic coat of fluidic material in which bioactive biomolecules are tethered via spacers. The amount of said internal biocompatible liquid core is adjusted so that said pliant membrane is partially collapsed and the corpuscle can take an amoebic shape. Alternatively; said pliant hydrophobic membrane is sandwiched between two hydrophilic layers, a coat and an underlay, of fluidic material. The proposed structure of said scaffold increases the ability of dynamic remodeling of said tethered biomolecules.

The method of production of the proposed multivalent biologic constructs comprises preparing the favorable biomolecules, mostly recombinant proteins or functional frictions of proteins prepared by recombinant technology using bacterial or eukaryotic cells, are tethered to an anisometric scaffold using spacers to produce multivalent biologic constructs of said biomolecules. The proposed invention is about recruitment of the relatively unstable monomeric, monovalent bioactive biomolecules that involve in cell signaling, into stable multivalent forms via fixing them, via spacers or linkers, into a scaffold to form MBCs that can be used to induce and/or augment a therapeutic effect. Thus; the produced MBCs are more stable and have a higher functional affinity due to multivalency.

These superiorities can be used to produce agonists; wherein an MBC interacts simultaneously with multiple corresponding receptors of a target cell. Said multiple interactions induce augmented signal which is transduced into a potentiated therapeutic effect and/or overcomes cellular resistance. On the other hand; the high functional affinity of the proposed MBCs can be employed for competitive inhibition; wherein an MBC simultaneously occupies multiple binding sites to competitively inhibit a target ligand.

Besides; the proposed multivalent constructs are capable, via using the integrated functional domains, of performing a consumptive inhibition. The stability and multivalency of said construct can be employed to consume circulating molecules of a target ligand, so that consumptively inhibit said ligand and spare its corresponding receptors. The saturated consumptive MBCs are then removed from the circulation of a recipient by the reticuloendothelial system. These proposed consumptive inhibitors don't target cell receptors; so they have a higher therapeutic index.

Additionally; the composite nature of the proposed MBCs opens the door for manipulation of the substructure of said MBCs. These maneuvers can apply specific characteristics on the MBC to achieve a desirable effect. As an example; the scaffold of the MBC can be a core of streptavidin, which has a higher affinity to anchor the activated platelets via the RYD sequence which mimics the RGD receptor domain of fibronectin. This characteristic can be useful in increasing the affinity of thrombolytic MBCs to the newly formed thrombus to decrease the bleeding side effect.

Moreover; the preparation of the proposed MBCs can involve a complexing procedure; wherein additional bioactive molecules can be attached to the scaffold to potentiate the therapeutic effect of the proposed MBCs; as an example, complexing more potent subunit vaccines. An immunogenic biomolecule can be tethered to a scaffold along with multiple antigenic recombinant proteins of a microbe, which are also tethered to said scaffold. Besides; a non-pathogenic segment of the genome of said microbe is also conjugated to said scaffold to form a multivalent vaccine construct. Said immunogenic biomolecule is a potent attractor for antigen presenting cell.

Additionally; the method of preparation of the proposed multivalent biologic construct can be further applied to form a wide array of direct immunomodulators to manipulate the immune system, altering the immune response to a desired level. Said immunomodulators can be also prepared by tethering favorable immunoactive recombinant proteins to a granular and/or corpuscular scaffold. These immunomodulators are introduced to an immune system where they exert a controllable direct augmentation or inhibition of the adaptive immune response towards a specific antigen.

Mainly; the proposed constructs are used, in vivo, to yield a therapeutic immunoinhibition. A monospecific multivalent biologic construct interacts simultaneously with multiple corresponding receptors presented by an immune cell to give the main signal without simultaneous costimulation leading to anergy, besides competitive inhibition of the native ligand of said receptors impeding the normal signaling pathway. Also; the proposed constructs can be used, in vivo, to yield a therapeutic immuno-stimulation. A polyspecific multivalent biologic construct interacts simultaneously with multiple corresponding receptors presented by an immune cell to give the main signal with simultaneous costimulation leading to activation. In vivo immuno-inhibition is easier and more practical than in vivo immuno-stimulation using synthetic modulators. In contrast to anergetic inhibition; stimulation of a subset of immune cells is subjected to many checkpoints within a specific microenvironment.

DETAILED DESCRIPTION OF THE DRAWINGS

Figure 1:
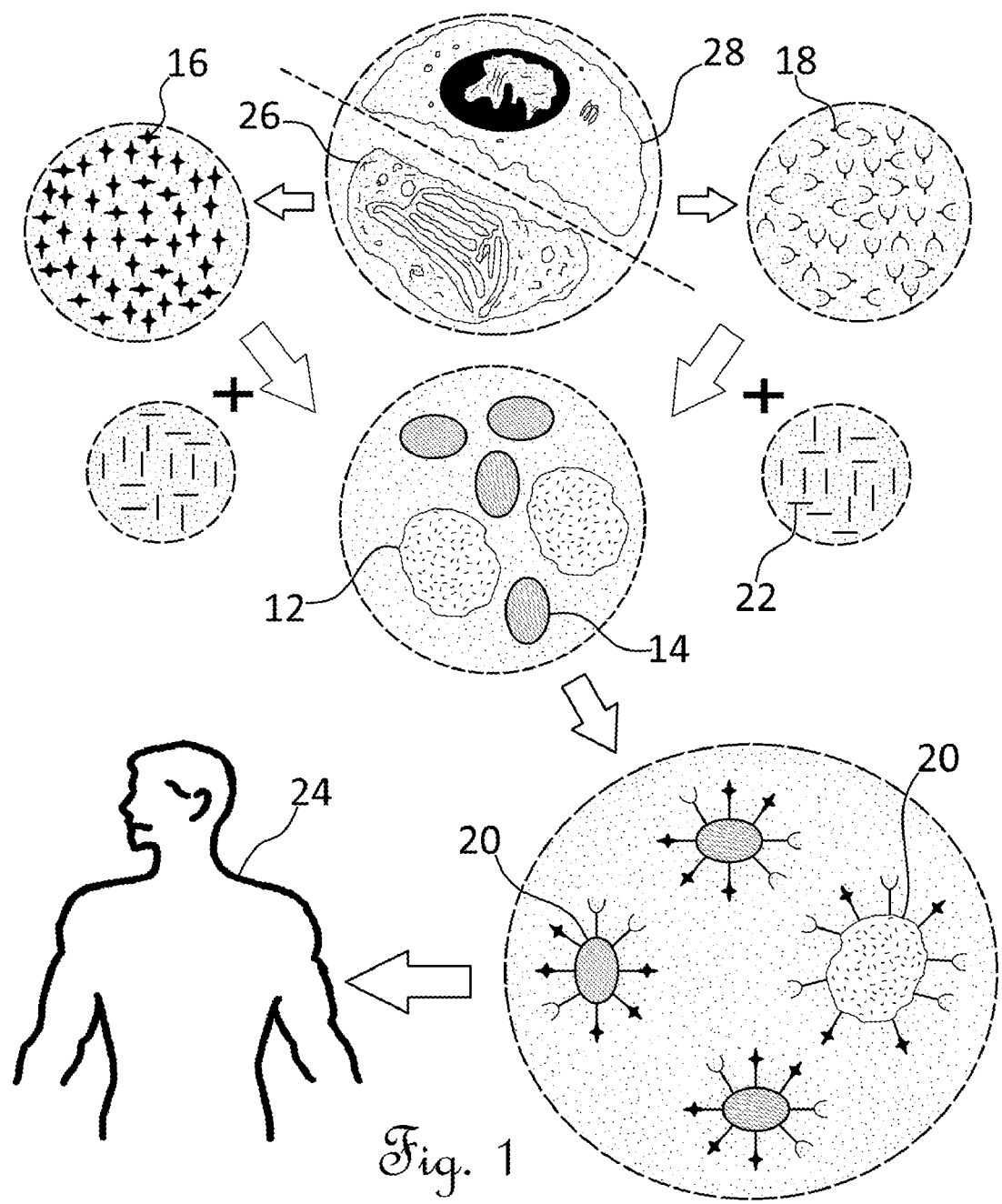
FIG. 1 is a schematic description of the basic preparation method of the proposed multivalent biologic constructs (MBCs).

Referring to the drawings in more details; they describe the method of preparation, the structure and the mechanism of action, with consequent advantages, of the proposed multivalent biologic constructs to induce a therapeutic modulation of cell response. A basic model is described in FIG. 1, FIG. 2, FIG. 3A and FIG. 3B; followed by different examples of using said multivalent biologic constructs to achieve various therapeutic actions, as described in the rest of the figures.

As a basic method of preparation of multivalent biological constructs (MBCs); favorable soluble biomolecules, mostly recombinant proteins or functional frictions of proteins prepared by recombinant technology using bacterial or eukaryotic cells, are tethered to an anisometric scaffold, via spacers or linkers, to produce multivalent biologic constructs of said biomolecules. The MBCs are then administered to a recipient to exert a therapeutic action and modulate cellular response. FIG. 1 is an example that describes said basic preparation method; the figure shows two soluble recombinant proteins, X-proteins 16 and Y-proteins 18, which are prepared using recombinant technology in bacterial 26 or eukaryotic 28 cells. Both recombinant X-proteins 16 and Y-proteins 18 are then tethered, via spacers 22, to two different forms of scaffolds to form a multivalent X/Y-protein biologic constructs 20, hereinafter called MBCs-X/Y 20. Said scaffolds are non-spherical micro-/nano-scale granules 14 and/or micro-/nano-scale corpuscles 12. MBCs-X/Y 20 are then administered via a suitable route of administration into a recipient 24 to exert a desirable therapeutic action.

Figure 2:
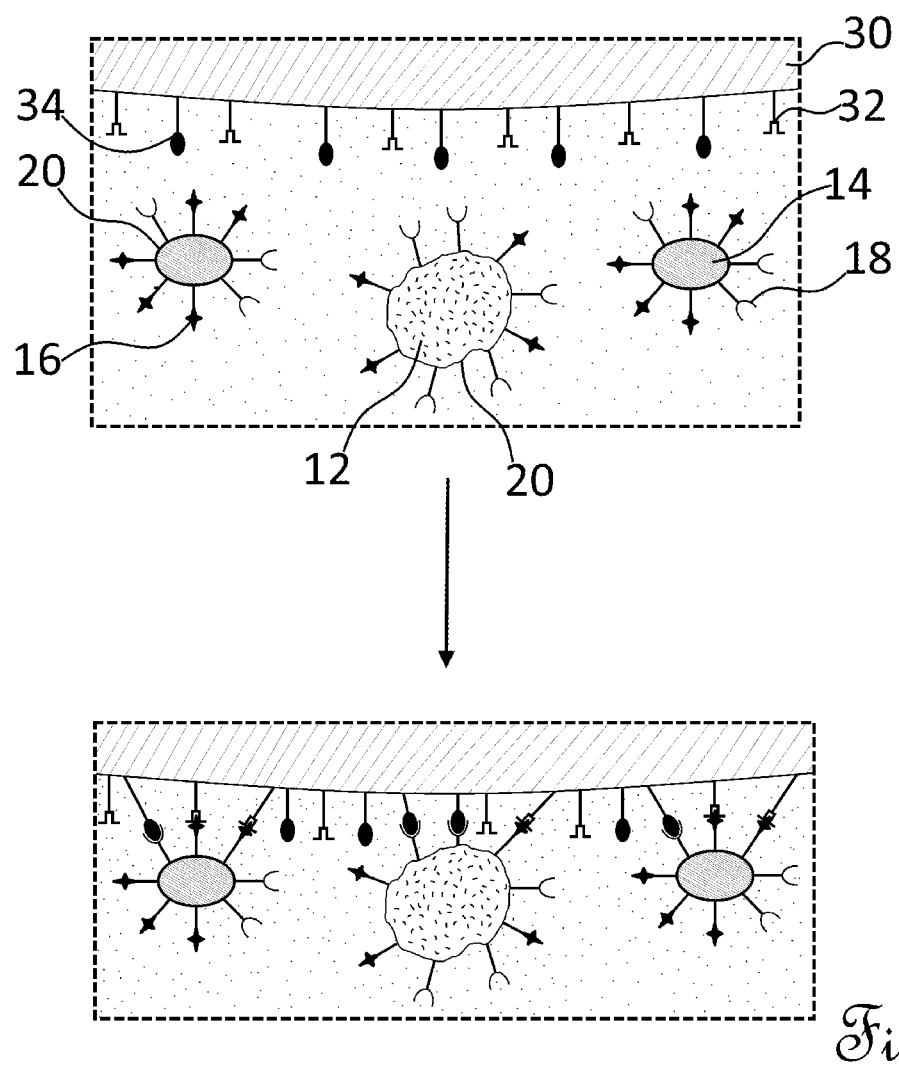
FIG. 2 is a schematic description of the basic interaction between said multivalent biologic constructs (MBCs) and a target cell.

FIG. 2 is a schematic description showing the basic mechanism of action of multivalent biologic constructs. The figure describes the interaction between a target cell 30 and MBCs-X/Y 20. In the upper portion of the figure; Said target cell 30 presents surface receptors, as X-protein receptor 32 and Y-protein receptors 34, while MBCs-X/Y 20 present multiple ligands, X-protein 16 and Y-protein 18 ligands, tethered to a scaffold of micro-/nano-scale granules 14 and a scaffold of micro-/nano-scale corpuscles 12. In the lower portion of the figure; each of said MBCs-X/Y 20 interacts simultaneously with multiple X-protein receptors 32 and multiple Y-protein receptors 34 of said target cell 30.

Figure 3A:
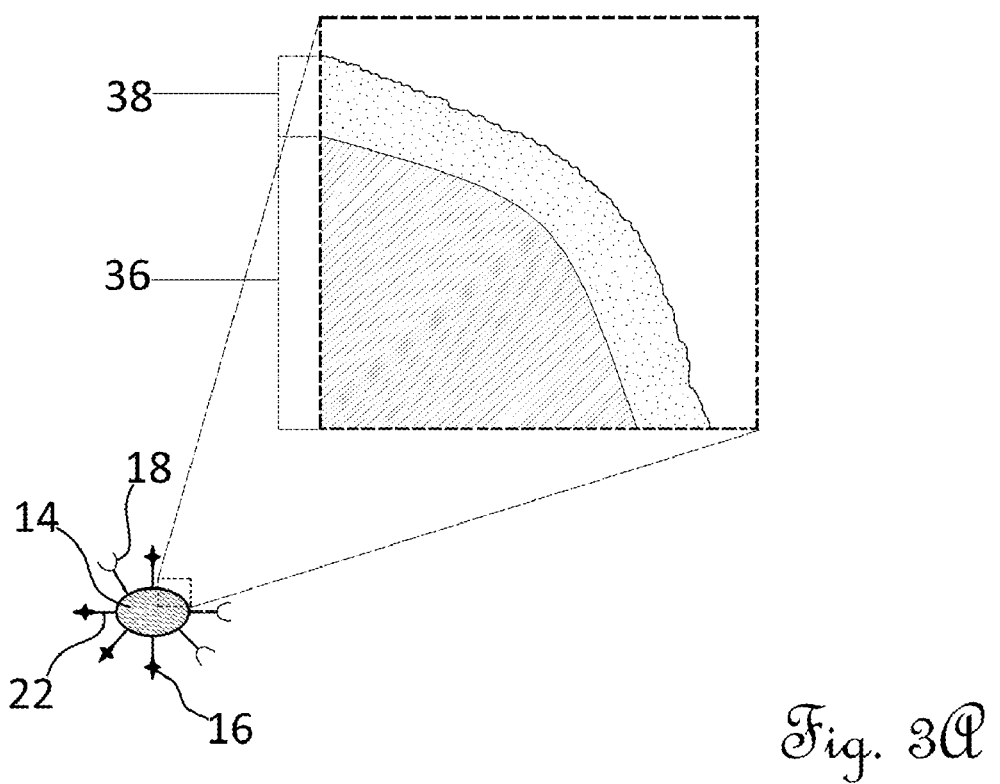
FIG. 3A is a schematic description showing the structure of the granular scaffold of a multivalent biologic construct (MBC).

FIG. 3A is a schematic description showing the basic structure of granular scaffolds of MBCs. The structure of a micro- or nano-scale granule 14 comprises a non-spherical anisometric hydrophobic polymeric core 36 of a biocompatible, biodegradable substance, coated with a hydrophilic coat 38 of fluidic material in which bioactive biomolecules are tethered via spacers 22. Said structure increases the ability of dynamic remodeling of said bound biomolecules. As a model; FIG. 3A describes a granule 14 which comprises a non-spherical polymeric core 36 of PLGA copolymer coated with PEG coat 38 of suitable molecular weight. The degree of fluidity of said PEG coat 38 can be monitored by the molecular weight of PEG molecules. Bioactive recombinant X-proteins 16 and Y-proteins 18 are tethered, via spacers 22, to the PEG coat 38; increasing surface mobility of said bound X-proteins 16 and Y-proteins 18.

Figure 3B:
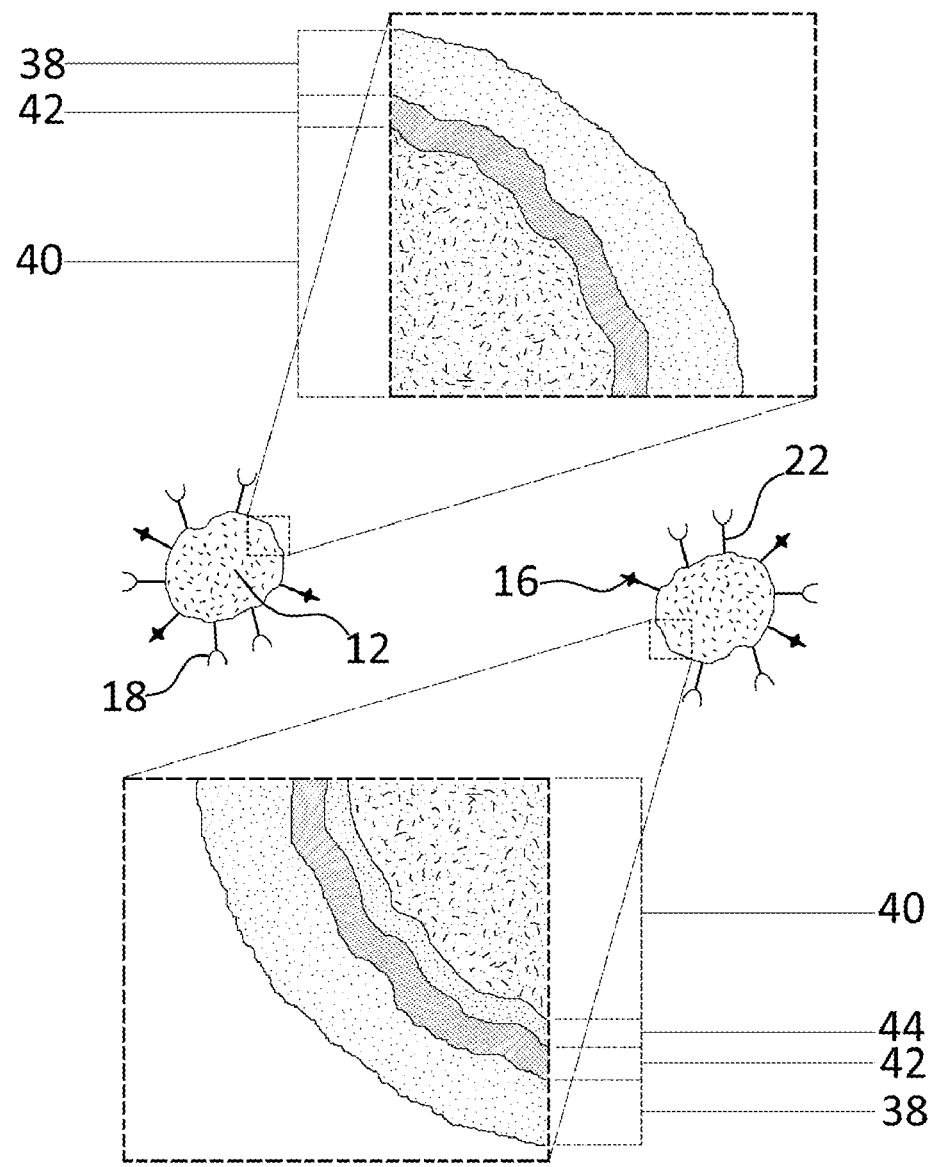
FIG. 3B is a schematic description showing different embodiments of the structure of the corpuscular scaffold of a multivalent biologic construct (MBC).

FIG. 3B is a schematic description showing different embodiments of the basic structure of corpuscular scaffolds of MBCs. In one basic embodiment; the structure of a micro- or nano-scale corpuscle 12 comprises an internal biocompatible liquid core 40 contained within a thin, flexible, pliant biodegradable hydrophobic membrane 42, coated with a hydrophilic coat 38 of fluidic material in which bioactive biomolecules are tethered via spacers 22. The amount of said internal biocompatible liquid core 40 is adjusted so that said pliant membrane 42 is partially collapsed and the corpuscle 12 can take an amoebic shape. In another basic embodiment; said pliant hydrophobic membrane 42 is sandwiched between two hydrophilic layers, a coat 38 and an underlay 44, of fluidic material. As a model; FIG. 3B describes a corpuscle 12 which comprises an aqueous core 40 contained within a pliant PLGA membrane 42 which coated with suitable molecular weight PEG coat 38. And in another model; said pliant PLGA membrane 42 is sandwiched between to two layers, a coat 38 and an underlay 44, of suitable molecular weight PEG molecules to formulate PEG-PLGA-PEG triblock. Bioactive recombinant X-proteins 16 and Y-proteins 18 are tethered, via spacers 22, to the PEG coat 38 providing unrestricted surface mobility of said bound X-proteins 16 and Y-proteins 18.

Basic Advantages

The multivalency of the proposed constructs helps simultaneous multiple binding interactions between the multiple ligands presented by said constructs with their target receptors. As Individual binding events increase the probability of other interactions to occur between the unbound ligands of said constructs and their corresponding binding sites; due to an increase in the local concentration of each binding ligand in proximity to the corresponding binding site. Individually, each binding interaction may be readily broken; however, when many simultaneous binding interactions are present, the transient unbinding of a single site does not allow the molecule to diffuse away, and binding of that weak interaction is likely to be restored.

So, the multivalency of the proposed constructs results in a stable construct-cell adhesion by increase the avidity of the ligand-receptor non-covalent binding. Additionally; simultaneous multiple binding interactions between the multiple ligands presented by said constructs with their target receptors, augment cell response by magnifying the transduced signal. Moreover; different ligands can be presented simultaneously by said constructs, so MBCs can be monospecific if the presented ligands are identical, or polyspecific if the presented ligands are non-identical. The proposed structure is more biomimetic and may be essential for achieving the desired therapeutic effect as in case of immunomodulation; wherein more than one signal is needed at the same time to accomplish cell activation.

The structure of biodegradable scaffolds of MBCs is advantageous. The core can attain a therapeutic function by conjugating drugs and other bioactive substances with PLGA molecules. The flexibility provided by the spacers and the fluidic nature of PEG coat enables unrestricted mobility of the bound biomolecules facilitating clustering and redistribution, which help decrease the steric hindrance and increase the avidity due to increasing the availability of binding ligands to their corresponding receptors.

Additionally; PEG coat is more stable than lipid bilayers which have poor stability due to lipid exchange between liposomes and cells (van der Weijden et al; 2014). Moreover; PEG hydrophilic coat increases solubility, decreases immunogenicity and antigenicity, shields the MBCs from recognition by RES and inhibit non-specific interaction and opsonization, leading to reduction of MBCs clearance and increase the circulatory time (Knop et al; 2010). Yet; the side effects resulting from the proposed structure of MBCs may include hypersensitivity reaction to the structural components, changes in the pharmacokinetic behavior and non-biodegradability of PEG coat. Also, the side product may have variable degrees of side effects which are usually limited with the use of pharmaceutical grade components.

The pliable amoebic shape of corpuscular scaffolds mimics the natural cells geometrically and increases the surface contact area. Additionally; drugs and other bioactive substances can be loaded into the liquid core of the corpuscular scaffold. Moreover; the liquid core of the corpuscular scaffold can be a biocompatible ferrofluid, forming ferromagnetic MBCs which can be guided via magnetic fields to target specific areas. The pliant structure of the corpuscular scaffolds facilitates migration of said ferromagnetic MBCs towards target sites.

Figure 4:
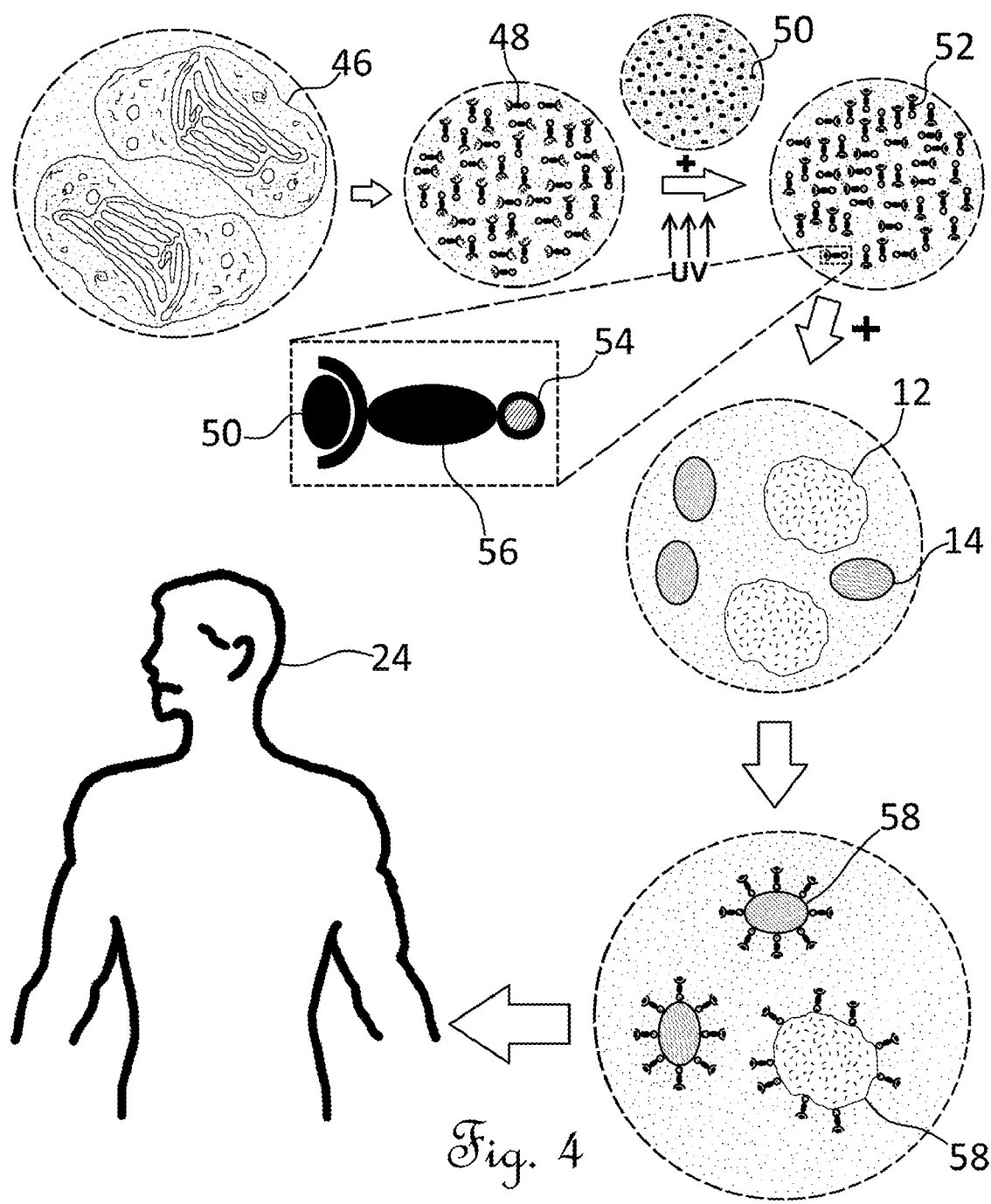
FIG. 4 is a schematic description of the method of preparation of multivalent pMHC class I biologic constructs (MBCs-pMHC class I).
Figure 5:
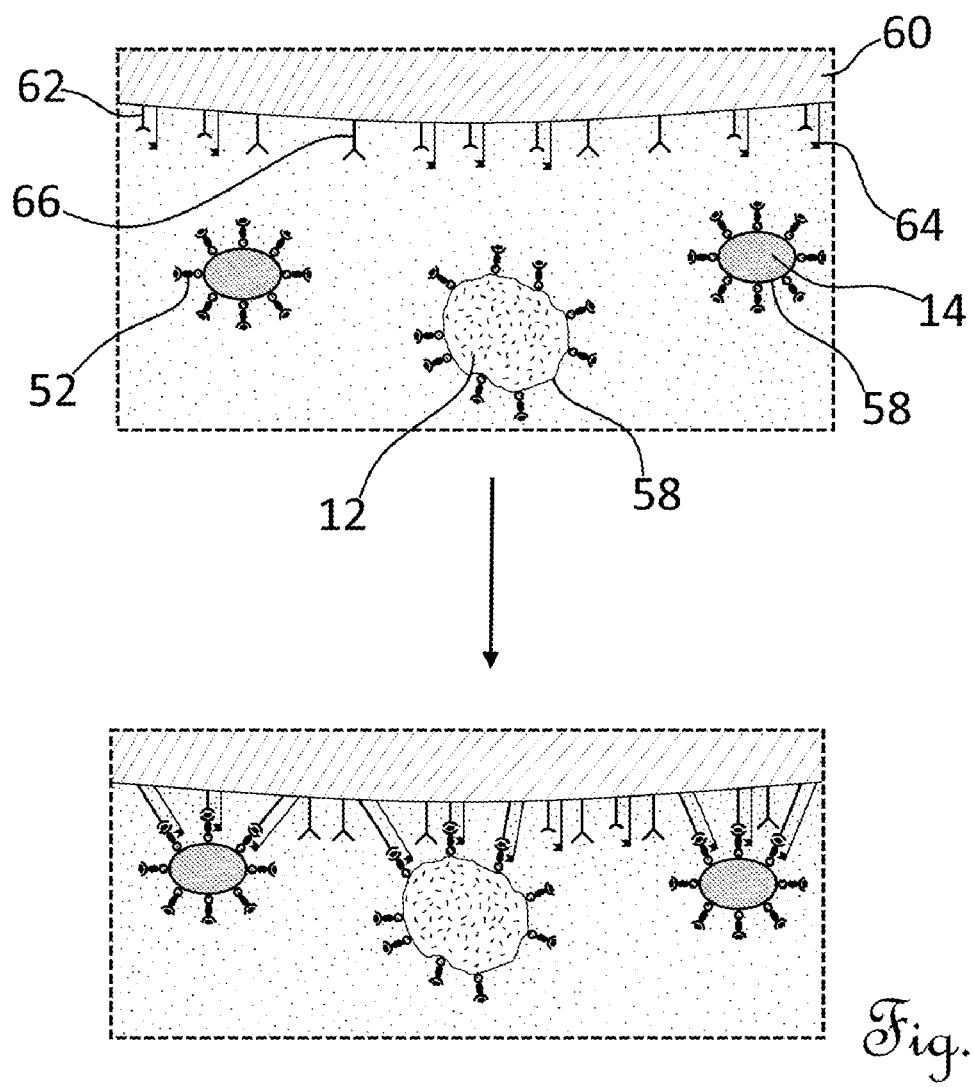
FIG. 5 is a schematic description of the interaction between T-cytotoxic cell and multivalent pMHC class I biologic constructs (MBCs-pMHC class I).
Figure 6:
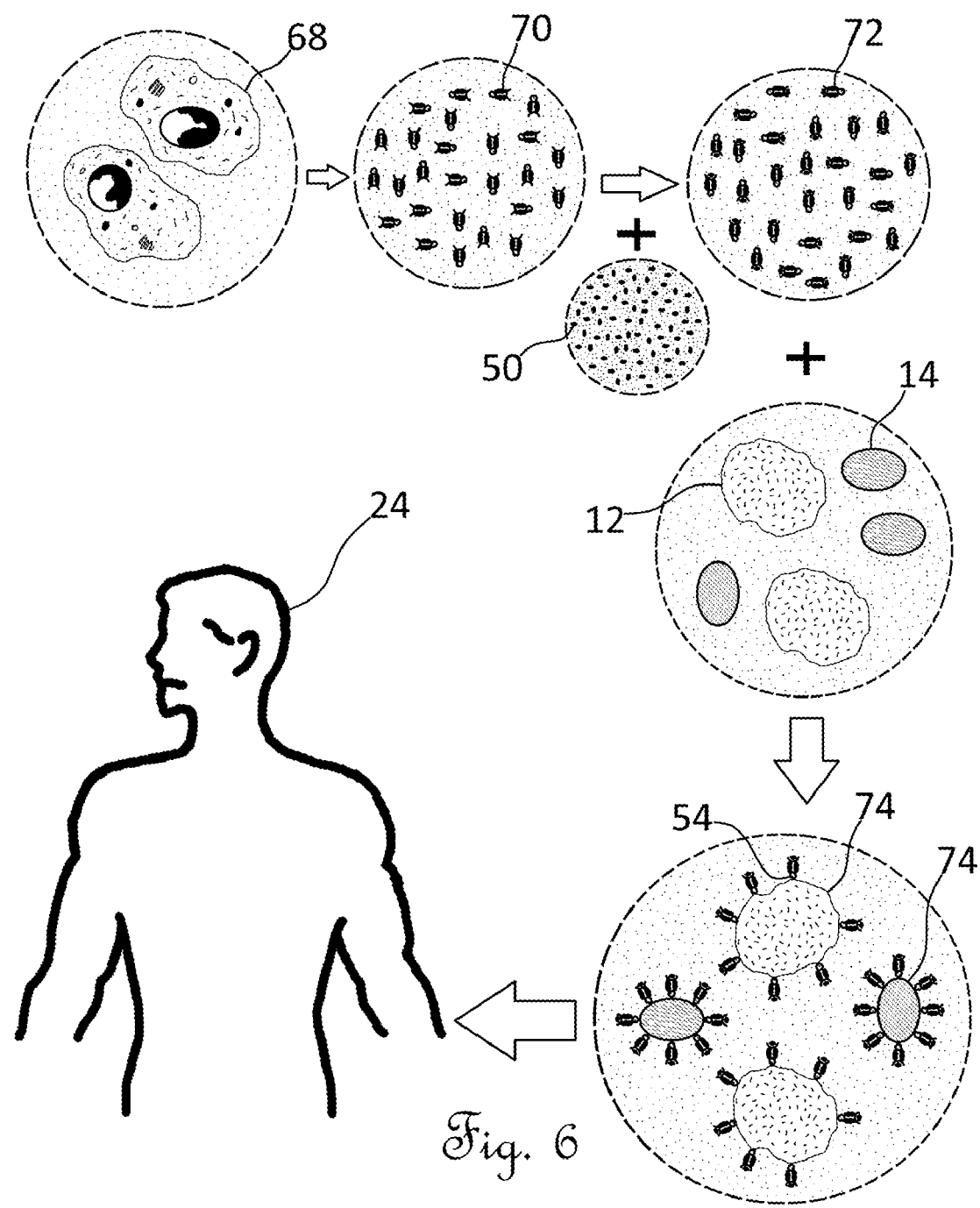
FIG. 6 is a schematic description of the method of preparation of multivalent pMHC class II biologic constructs (MBCs-pMHC class II).
Figure 7:
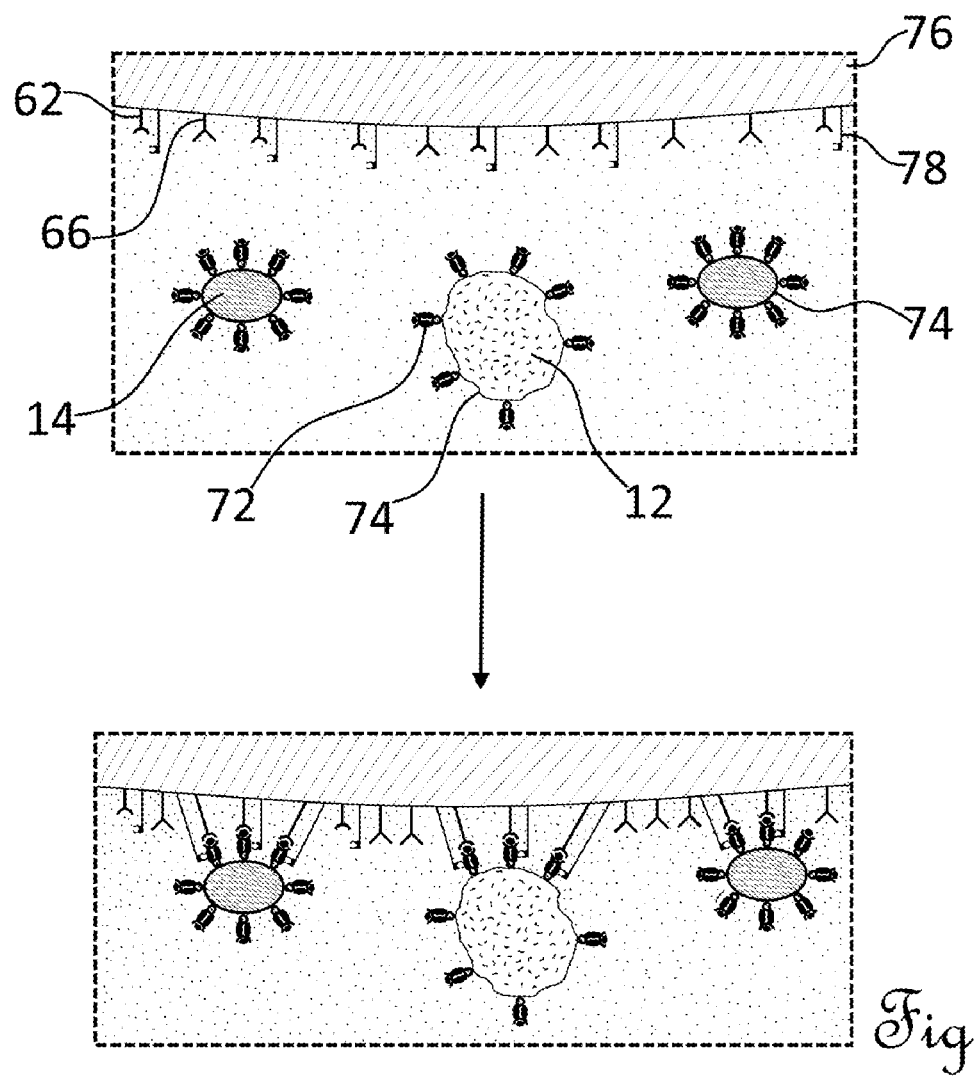
FIG. 7 is a schematic description of the interaction between T-helper cell and multivalent pMHC class II biologic constructs (MBCs-pMHC class II).

FIG. 4 and FIG. 5 are schematic descriptions showing the method of preparation and mechanism of action of multivalent pMHC class I biologic constructs 58, hereinafter called MBCs-pMHC class I 58. Both figures describe an example of the application of the proposed multivalent biologic constructs to inhibit cell-mediated immunity. As shown in FIG. 4; the preferred embodiment of the preparation process of MBCs-pMHC class I 56 involves expressing a plurality of recombinant MHC class I molecules 56 in *E. coli* prokaryotes 46 (Garboczi et al, 1992). Said recombinant MHC class I molecules 56 are refolded with allele-specific conditional UV-sensitive peptide to form conditional peptide-MHC class I 48. Then; UV-mediated peptide exchange process takes place in a time-dependent manner (Rodenko et al, 2006); wherein exposure to UV rays cleaves the conditional UV-sensitive peptides and the empty, peptide receptive MHC molecules are rescued by the presence of self-antigenic peptides 50 derived from a recipient 24 who suffer autoimmune disease. The former process produces peptide-MHC class I complexes 52 which then conjugated via linkers 54 to the proposed granular 14 and/or corpuscular 12 scaffolds. The resultant MBCs-pMHC class I 58 can be given via a suitable route of administration to said recipient 24 to induce a therapeutic action in the form of neutralization of a plurality of high-affinity autoreactive T-cytotoxic (Tc) cells by reestablishing of an anergetic Tc cell pool.

FIG. 5 describes the mechanism of action and advantages of said MBCs-pMHC class I 58. The figure is a schematic description of the interaction between part of Tc cell 60 and the MBCs-pMHC class I 58. In the upper portion of the figure; Said part of Tc cell 60 presents surface receptors, such as T cell receptors 62 (TCRs) along with CD8 markers 64 in addition to CD28 markers 66, while MBCs-pMHC class I 58 present multiple pMHC class I ligands 52 tethered to a scaffold of micro-/nano-scale granules 14 and/or a scaffold of micro-/nano-scale corpuscles 12. In the lower portion of the figure; each of said MBCs-pMHC class I 58 interacts simultaneously with multiple TCR 62 along with CD8 markers 64 presented by said Tc cell 60. This interaction gives an antigen-specific main stimulatory signal 1, while the Tc cell 60 lacks simultaneous costimulation of the CD28 markers 66. The introduction of the main stimulatory signal 1 without simultaneous costimulation for said Tc cell 60 leads to anergy; wherein Tc cell 60 are unable to mount an effective cellular immunological response against its target. Additionally; MBCs-pMHC class I 58 occupy native TCRs 62 presented by host Tc cells 60, and thus competitively inhibit the natural interaction between host nucleated cells (not shown) and host Tc cells 60.

Advantages: in addition to the basic advantages provided by the proposed structure of the multivalent biologic constructs; MBCs-pMHC class I neutralize a portion of the cytotoxic T cell pool via two mechanisms; anergy and competitive inhibition. Potential therapeutic applications of said MBCs-pMHC class I are autoimmune diseases and graftversus-host disease.

FIG. 6 and FIG. 7 are schematic descriptions showing the method of preparation and mechanism of action of multivalent pMHC class II biologic constructs 74, hereinafter called MBCs-pMHC class II 74. Both figures describe an example of the application of the proposed multivalent biologic constructs to inhibit adaptive immunity. FIG. 6 describes the method of preparation of said MBCs-pMHC class II 74. A variety of expression systems have been used to prepare recombinant pMHC class II complexes 72 (Vollers and Stern; 2008), and the figure describes the most common protocol. It involves coexpression of α- and β-subunits of MHC class II molecules 70 in baculovirus-infected (Stern and Wiley; 1992) or stably transformed insect cells 68 (Sloan et al; 1995); yielding peptide-free molecules 70 which can be isolated and loaded with self-antigenic peptides 50 derived from a recipient 24 who suffer autoimmune disease, in vitro. This expression approach of recombinant MHC class II proteins 70 depends on lack of antigen processing and loading machinery in insect cells 68. The former process produces pMHC class II complexes 72 which then conjugated via linkers 54 to the proposed granular 14 and/or corpuscular 12 scaffolds. The resultant MBCs-pMHC class II 74 can be given via a suitable route of administration to said recipient 24 to induce a therapeutic action in the form of neutralization of a plurality of high-affinity T-helper (Th) cells by establishing an anergetic Th cell pool.

FIG. 7 describes the mechanism of action and advantages of said MBCs-pMHC class II 74. The figure is a schematic description of the interaction between part of Th cell 76 and the MBCs-pMHC class II 74. In the upper portion of the figure; Said part of Th cell 76 presents surface receptors, such as T cell receptors 62 (TCRs) along with CD4 markers 78 in addition to CD28 markers 66, while MBCs-pMHC class II 74 present multiple pMHC class II ligands 72 tethered to a scaffold of micro-/nano-scale granules 14 and a scaffold of micro-/nano-scale corpuscles 12. In the lower portion of the figure; each of said MBCs-pMHC class II 74 interacts simultaneously with multiple TCRs 62 along with CD4 78 markers presented by said Th cell 76. This interaction gives an antigen-specific main stimulatory signal 1, while said Th cell 76 lacks simultaneous costimulation of the CD28 markers 66. The introduction of the main stimulatory signal 1 without simultaneous costimulation for the Th cell 76 leads to anergy; wherein the Th cell 76 are unable to mount an effective immunological response. Additionally; MBCs-pMHC class II 74 simultaneously occupy native TCRs 62 presented by host Th cells 76, and so competitively inhibit the natural interaction between host antigen presenting cells (not shown) and host Th cells 76. Moreover; competitive inhibition of native TCRs 62 presented by the host Th cells 76 by means of MBCs-pMHC class II 74, hinders the T cell-dependent activation of follicular B cells (not shown).

Advantages: in addition to the basic advantages provided by the proposed structure of the multivalent biologic constructs; MBCs-pMHC class II neutralize a portion of the helper T cell pool via two mechanisms; anergy and competitive inhibition. Anergetic Th cells not only lose effector immunological response, but also tend to secrete anti-inflammatory mediators such as IL-10. Potential therapeutic applications of said MBCs-pMHC class II are autoimmune diseases and graft-versus-host disease.

Figure 8:
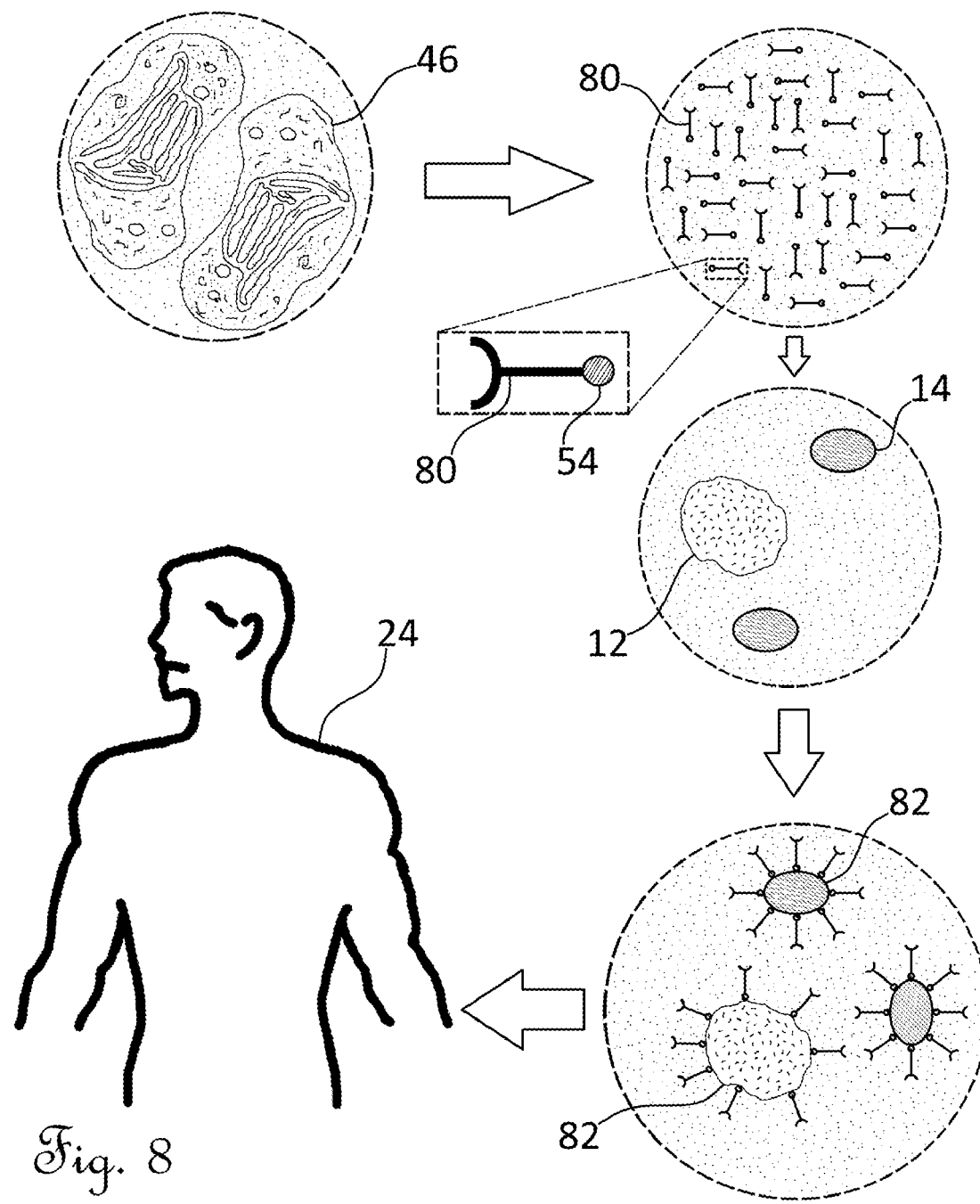
FIG. 8 is a schematic description of the method of preparation of multivalent TCR biologic constructs (MBCs-TCR).
Figure 9:
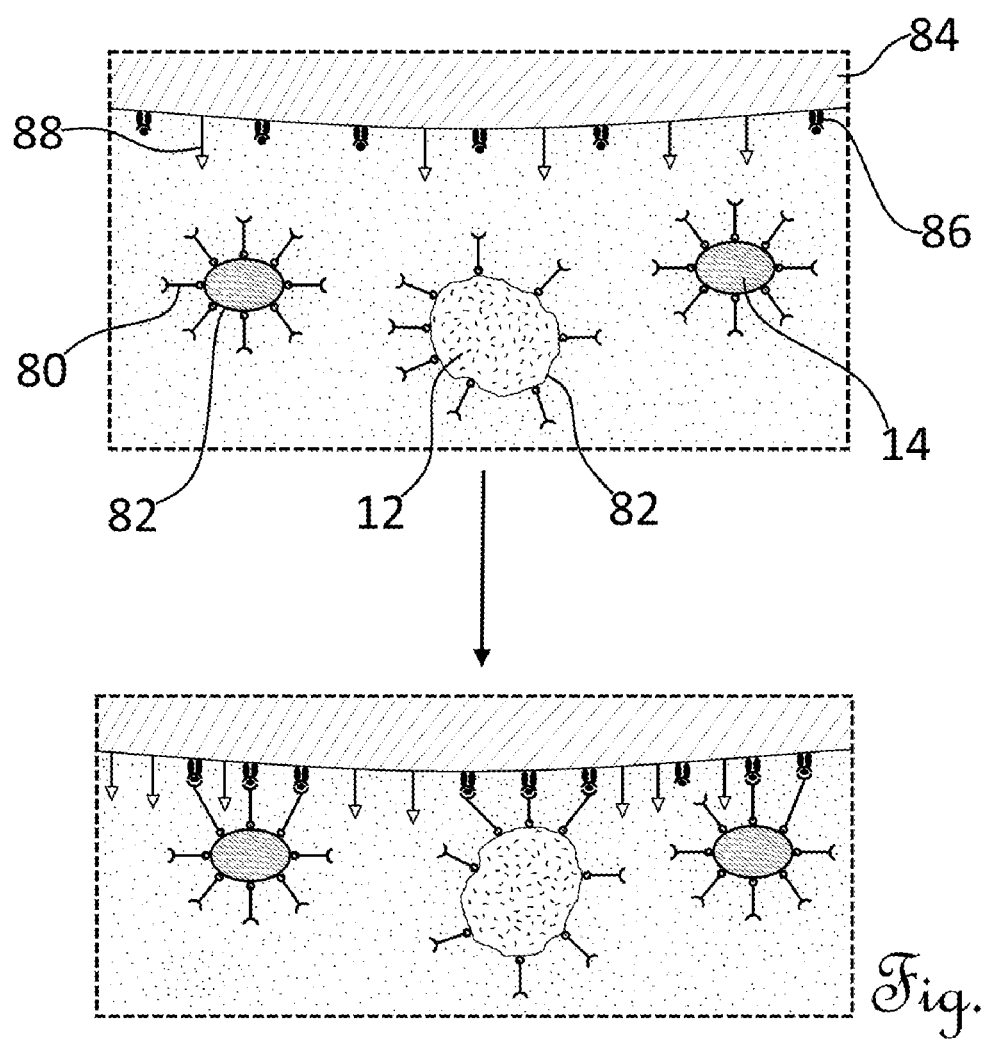
FIG. 9 is a schematic description of the interaction between follicular B cell and multivalent TCR biologic constructs (MBCs-TCR).

FIG. 8 and FIG. 9 are schematic descriptions showing the method of preparation and mechanism of action of multivalent TCR biologic constructs 82, hereinafter called MBCs-TCR 82. Both figures describe an example of the application of the proposed multivalent biologic constructs to inhibit humoral immunity. As shown in FIG. 8; the preferred embodiment of the preparation process of MBCs-TCR 82 involves the expression of α and β chains of recombinant TCR protein 80 separately in E. coli 46 prokaryotes and pair said chains by a non-native disulfide bond to yield pluralities of recombinant TCR molecules 80 (Boulter et al; 2003). Said recombinant TCR molecules 80 are then conjugated via linkers 54 to the proposed granular 14 and/or corpuscular 12 scaffolds. The resultant MBCs-TCR 82 can be given via a suitable route of administration to a recipient 24 to induce a therapeutic action in the form of neutralization of pluralities of follicular B cells by establishing an anergetic B cell pool.

FIG. 9 describes the mechanism of action and advantages of said MBCs-TCR 82. The figure is a schematic description of the interaction between part of follicular B cell 84 and the MBCs-TCR 82. In the upper portion of the figure; Said part of follicular B cell 84 presents surface receptors, such as pMHC class II proteins 86 in addition to CD40 markers 88, while MBCs-TCR 82 present multiple recombinant TCR proteins 80 tethered to a scaffold of micro-/nano-scale granules 14 and a scaffold of micro-/nano-scale corpuscles 12. In the lower portion of the figure; each of MBCs-TCR 82 interacts simultaneously with multiple native pMHC class II proteins 86 presented by said follicular B cell 84. This interaction gives a main stimulatory signal 1, while the follicular B cell 84 lacks simultaneous costimulation of the CD40 markers 88. The introduction of the main stimulatory signal 1 without simultaneous costimulation for said follicular B cell 84 leads to anergy; wherein said follicular B cell 84 is unable to mount an effective humoral immunological response against its target. Additionally; this interaction competitively inhibits the natural interaction between host Th cells (not shown) and the follicular B cells 84 as MBCs-TCR 82 occupy native pMHC class II complexes 86 presented by said follicular B cells 84. Moreover; MBCs-TCR 82 impede immunological response of T cells (not shown); wherein MBCs-TCR 82 competitively inhibit the interaction of T cells, which presents native TCRs, with host APCs (not shown) and host nucleated cells (not shown), which presents native MHC class II and MHC class I proteins respectively.

Advantages: in addition to the basic advantages provided by the proposed structure of the multivalent biologic constructs; said MBCs-TCR neutralize a portion of the follicular B cell pool via two mechanisms; anergy and competitive inhibition. Potential therapeutic applications of said MBCs-TCR are autoimmune diseases and graft-versus-host disease.

Figure 10:
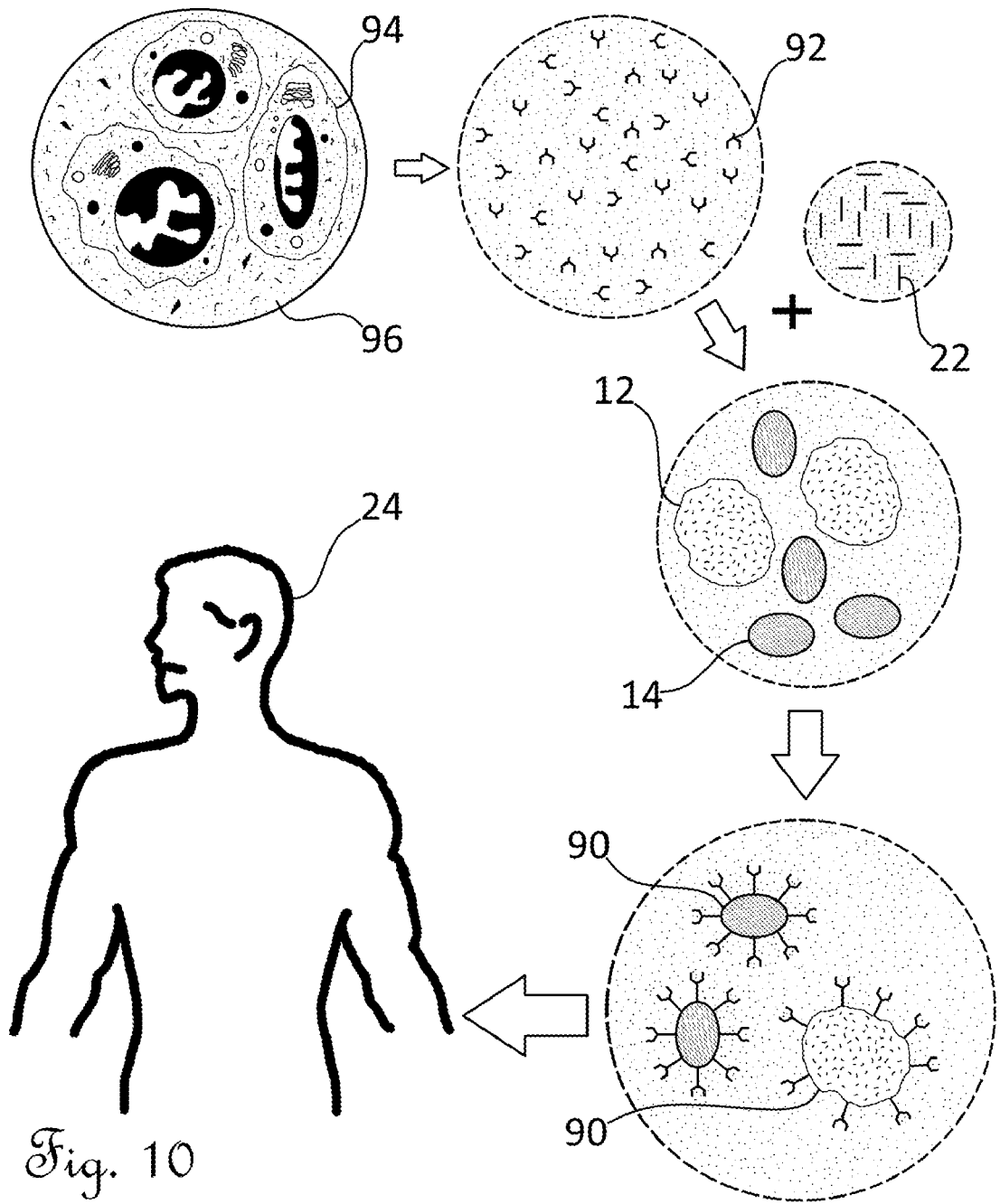
FIG. 10 is a schematic description of the method of preparation of multivalent anti-CD20 mAb biologic constructs (MBCs-antiCD20 mAb).
Figure 11:
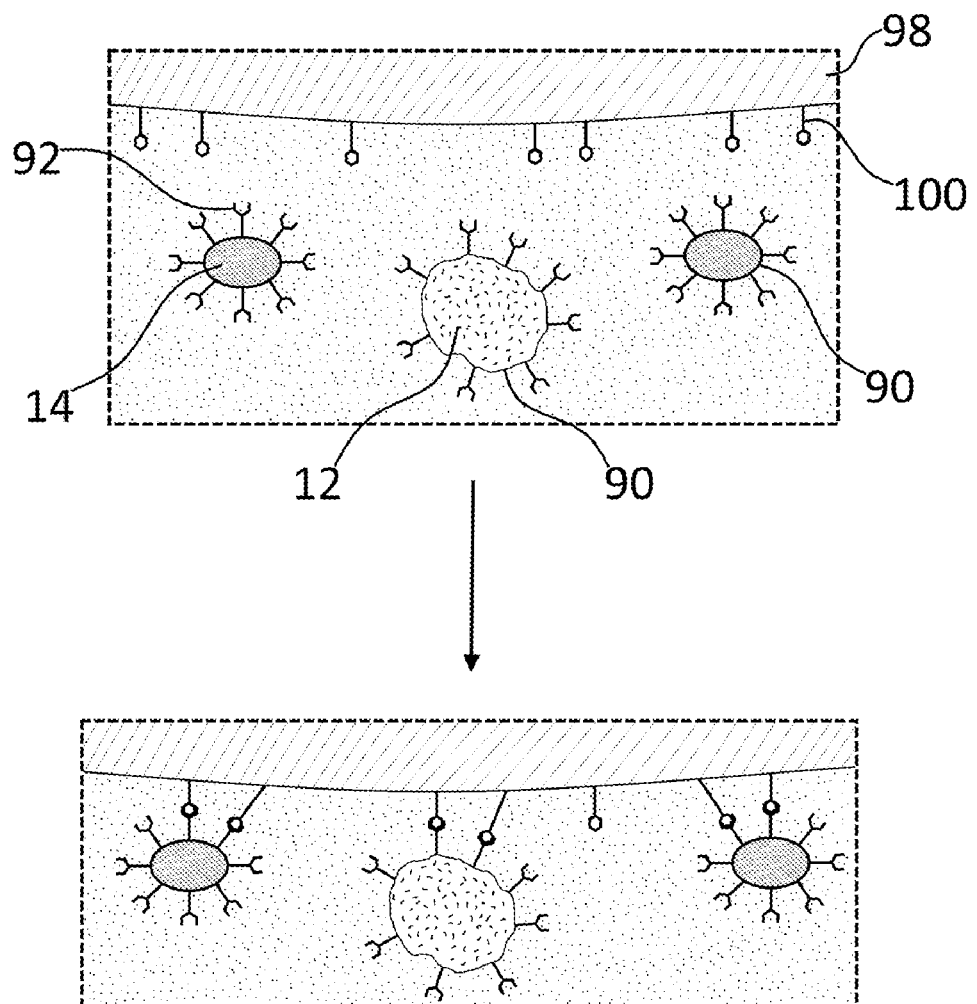
FIG. 11 is a schematic description of the interaction between a resistant cancerous B cell and multivalent anti-CD20 mAb biologic constructs (MBCs-antiCD20 mAb).

FIG. 10 and FIG. 11 are schematic descriptions showing the method of preparation and mechanism of action of multivalent anti-CD20 monoclonal antibodies biologic constructs 90, hereinafter called MBCs-antiCD20 mAb 90. Both figures describe an example of the application of the proposed multivalent biologic constructs to augment the therapeutic action of a signaling biomolecule on a resistant target cell, wherein the pathogenesis of the target cell resistance involves down-regulation of the corresponding receptors or decreasing the sensitivity of these receptors to said signaling biomolecule. The resistance of lymphoma to anti-CD20 therapy is a prominent example. FIG. 10 shows a schematic description of the method of preparation of MBCs-antiCD20 mAb 90. Anti-CD20 mAb 92 molecules can be prepared and purified using conventional preparation processes of mAb. The classical Hybridomas model is shown; wherein hybridoma cells 94 are cultured in HAT medium 96 and antiCD20 mAb 92 are harvested. Pluralities of said antiCD20 mAb 92 are conjugated via spacers 22 to the proposed granular 14 and/or corpuscular 12 scaffolds. The resultant MBCs-antiCD20 mAb 90 can be given via a suitable route of administration to a recipient 24, who is resistant to anti-CD20 mAb chemotherapy regimens, to induce an augmented therapeutic action in the form of cytotoxic or apoptotic effect on B cells.

FIG. 11 describes the mechanism of action of said MBCs-antiCD20 mAb 90. The figure is a schematic description of the interaction between MBCs-antiCD20 mAb 90 and a part of resistant cancerous B cell 98. In the upper portion of the figure; said part of cancerous B cell 98 presents a few CD20 antigens 100, while MBCs-antiCD20 mAb 90 present multiple anti-CD20 mAb 92 tethered to a scaffold of micro-/nano-scale granules 14 and a scaffold of micro-/nano-scale corpuscles 12. Said resistant cancerous B cell 98 presents fewer CD20 antigens 100 due to down-regulation of MS4A1 gene as a mechanism of cell resistance, besides altering the signaling pathway. In the lower portion of the figure; each of said MBCs-antiCD20 mAb 90 interacts simultaneously with multiple CD20 antigens 100 presented by said cancerous B cell 98. These simultaneous multiple interactions potentiate and prolong the therapeutic action of said multivalents 90 due to increasing avidity and the consequent signal magnification.

Advantages: in addition to the basic advantages provided by the proposed structure of the multivalent biologic constructs; said MBCs-antiCD20 mAb are superior to the monovalent chimeric antiCD20 mAb of the prior art and can overcome cellular mechanisms involving in the pathogenesis drug resistance via increasing functional affinity and signal magnification. Potential therapeutic applications of said MBCsantiCD20 mAb are resistant B-cell leukemias, lymphomas and autoimmune diseases.

Figure 12:
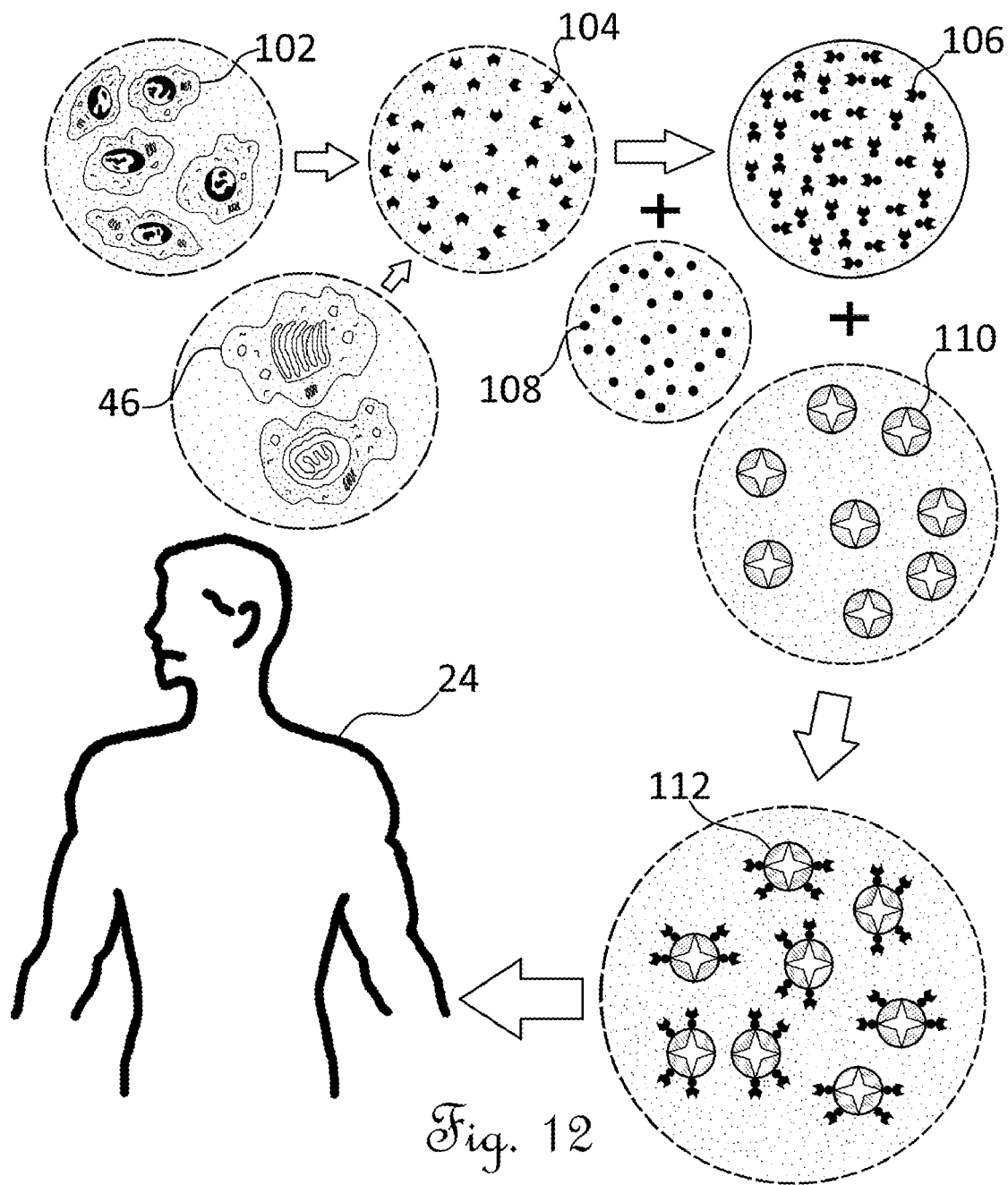
FIG. 12 is a schematic description of the method of preparation of multivalent urokinase biologic constructs (MBCs-UK).
Figure 13A:
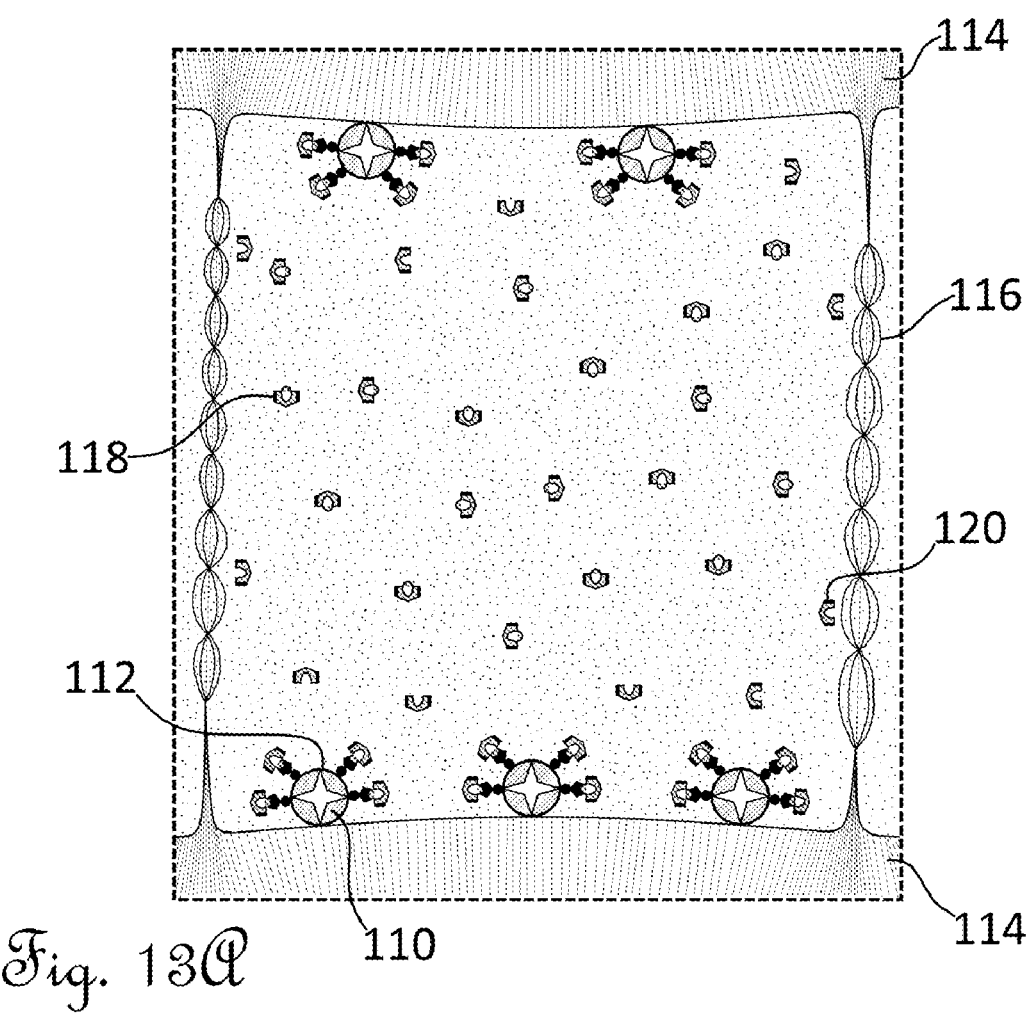
FIG. 13A is a schematic description of the interaction between multivalent urokinase biologic constructs (MBCs-UK) attached to an activated platelet and plasminogen molecules.
Figure 13B:
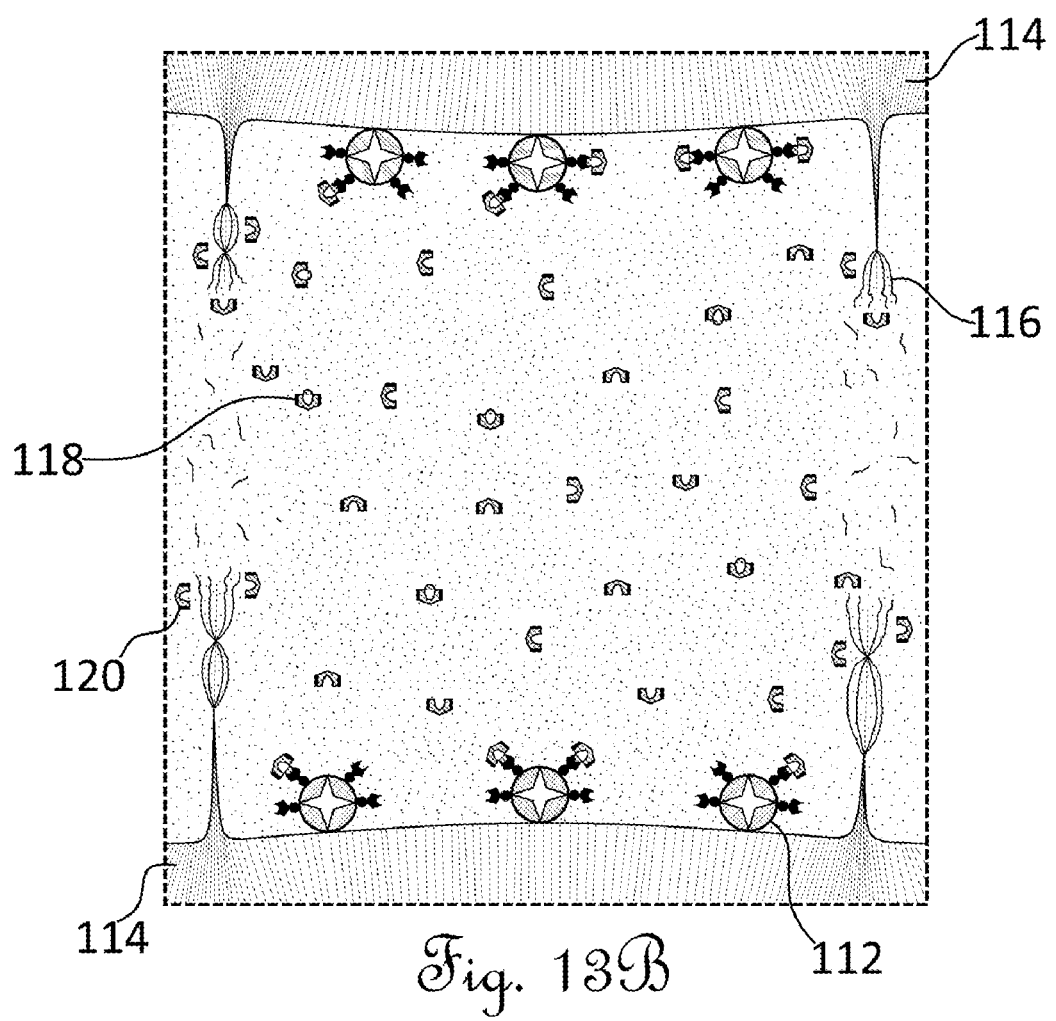
FIG. 13B is a schematic description of the targeted fibrinolytic effect of multivalent urokinase biologic constructs (MBCs-UK).

FIG. 12, FIG. 13A and FIG. 13B are schematic descriptions showing the method of preparation and mechanism of action of multivalent urokinase biologic constructs 112, hereinafter called MBCs-UK 112. The figures describe an example of the application of the proposed multivalent biologic constructs to augment the therapeutic action and improve the safety profile of thrombolytics. FIG. 12 shows a schematic description of the method of preparation of MBCs-UK 112. Urokinase 104 molecules can be prepared and purified using conventional preparation processes. Herein; urokinase 104 molecules can be isolated from human neonatal kidney cells 102 grown in tissue culture, or prepared recombinantly in E. coli 46 prokaryotes (Tang et al; 1997). Said urokinase 104 molecules are then biotinylated using biotin 108 to form biotinylated urokinase molecules 106; which are conjugated with a scaffold of streptavidin 110 to form MBCs-UK 112. Biotinylation process can be chemically or enzymatically performed. In enzymatic biotinylation; free biotin 108 molecules are linked to a specific lysine within a certain sequence, biotin acceptor peptide, by a bacterial biotin-ligase (Fairhead and Howarth; 2015). Whereas in chemical biotinylation; various conjugation chemistries are utilized to yield nonspecific biotinylation. Biotinylation is quick, specific and is unlikely to disturb the natural function of the urokinase proteins 104 due to the small size of biotin 108. Besides; biotin 108 binds to streptavidin 110 with an extremely high affinity, fast on-rate, and high specificity. The resultant MBCs-UK 112 can be given via a suitable route of administration to a recipient 24 to induce an augmented therapeutic action in the form of thrombolysis with lower bleeding risk.

FIG. 13A describes the mechanism of action of said MBCs-UK 112. The figure is a schematic description of the loading interaction between MBCs-UK 112 and activated platelets 114 along with interlacing fibrin 116; wherein the streptavidin 110 scaffold of said MBCs-UK 112 interacts with the surface of said activated platelets 114. The streptavidin 110 scaffold contains an RYD sequence which mimics the RGD receptor domain of fibronectin (Alon et al; 1990), so said scaffold 110 binds preferably and with high affinity with glycoprotein IIb/IIIa which presented extensively on the cell surface during platelet activation. Consequently, said activated platelets 114 are loaded with a large number of MBCs-UK 112 which activate plasminogen 118 to plasmin 120 with high functional affinity.

FIG. 13B describes the interaction between MBCs-UK 112 attached to an activated platelet 114 and plasminogen molecules 118 resulting in active plasmin molecules 120. The figure shows said activated platelets 114 loaded with multiple MBCs-UK 112. Each of said MBCs-UK 112 interacts simultaneously with a high functional affinity with multiple plasminogen molecules 118 which are directly activated into plasmin 120 that degrades fibrin 116 clots.

Advantages: The proposed MBCs-UK have multiple advantages over the monovalent urokinase of the prior art. Said multivalents have a higher functional affinity, as each of these multivalents can interact simultaneously with multiple plasminogen substrates turning them into active plasmin. Moreover; Said multivalents have more specificity, as the streptavidin scaffold sticks preferably to the cell surface of said activated platelet which results in more concentration of the effector drug in the site of action and thus increases the efficacy of the therapeutic action and decreases the bleeding side effect. Furthermore; said multivalents have a larger hydrodynamic size, which prolongs the circulatory time. Consequently; potential therapeutic applications of the proposed MBCs-UK are the treatment of myocardial infarction, ischemic stroke and massive pulmonary embolism as a more effective thrombolytic agent.

Figure 14:
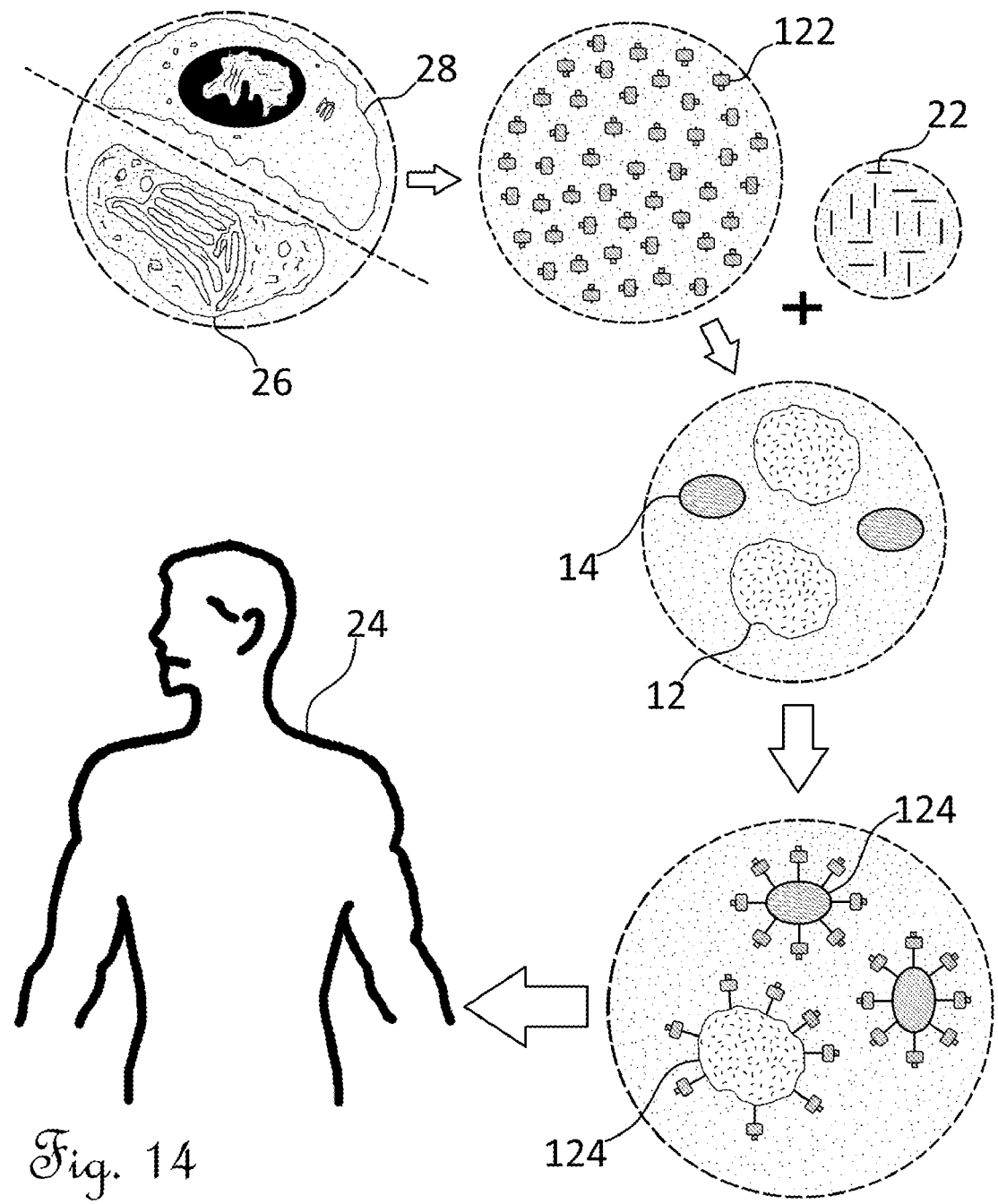
FIG. 14 is a schematic description of the method of preparation of multivalent IL-1 Ra biologic constructs (MBCs-IL1Ra).
Figure 15:
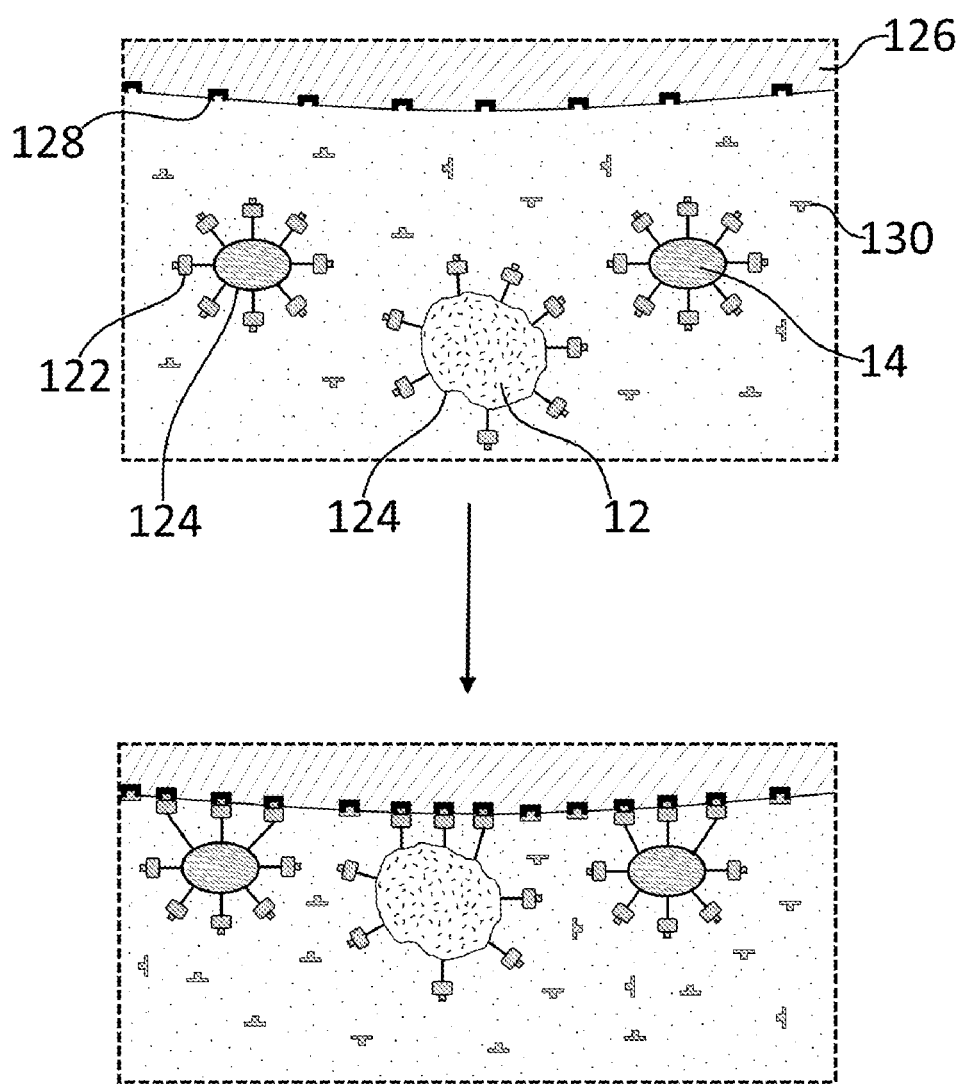
FIG. 15 is a schematic description of the interaction between multivalent IL-1 Ra biologic constructs (MBCs-IL1Ra) and an IL-1 target cell.

FIG. 14 and FIG. 15 are schematic descriptions showing the method of preparation and mechanism of action of multivalent interleukin 1 receptor antagonist biologic constructs 124, hereinafter called MBCs-IL1Ra 124. The figures describe an example of the application of the proposed multivalent biologic constructs as competitive inhibitors for a target cell receptor. FIG. 14 shows a schematic description of the method of preparation of MBCs-IL1Ra 124. Soluble IL-1Ra molecules 122, prepared by recombinant technology using bacterial 26 or eukaryotic 28 cells, are tethered via spacers 22 to a scaffold of micro-/nano-scale granules 14 and/or a scaffold of micro-/nano-scale corpuscles 12 to form MBCs-IL1Ra 124. Said MBCs-IL1Ra 124 can be given via a suitable route of administration to a recipient 24 to induce a therapeutic action in the form of competitive inhibition of Interleukin-1 molecules.

FIG. 15 describes the mechanism of action of said MBCs-IL1Ra 124. The figure is a schematic description of the interaction between MBCs-IL1Ra 124 and a part of IL-1 target cell 126. In the upper portion of the figure; said part of the IL-1 target cell 126 presents IL-1 receptors 128, while MBCs-IL1Ra 124 present multiple IL-1Ra molecules 122 tethered to a scaffold of micro-/nano-scale granules 14 and/or a scaffold of micro-/nano-scale corpuscles 12. MBCs-IL1Ra 124 compete with native IL-1 molecules 130 for said receptors 128. In the lower portion of the figure; each of said MBCs-IL1Ra 124 interacts simultaneously with multiple IL-1 receptors 128 presented by IL-1 target cell 126, depriving native IL-1 molecules 130 of their corresponding binding sites. This augmented competitive inhibition leads to a reduction of the proinflammatory effect of IL-1 molecules 130 which can be an improved therapeutic approach for many inflammatory diseases.

Advantages: besides the basic advantages provided by the proposed structure of the multivalent biologic constructs; said MBCs-IL1Ra are superior to monovalent recombinant IL-1 Ra molecules of the prior art, due to higher functional affinity, increased contact surface area (synapse area) and longer circulatory time. These advantages are vital for more efficient competitive inhibition, which is the mechanism of action of the effector drug. A potential therapeutic application of the proposed MBCs-IL1Ra is controlling rheumatoid arthritis in adults with moderately to severely active disease who have an inadequate response to therapy with one or more disease-modifying antirheumatic drugs.

Figure 16:
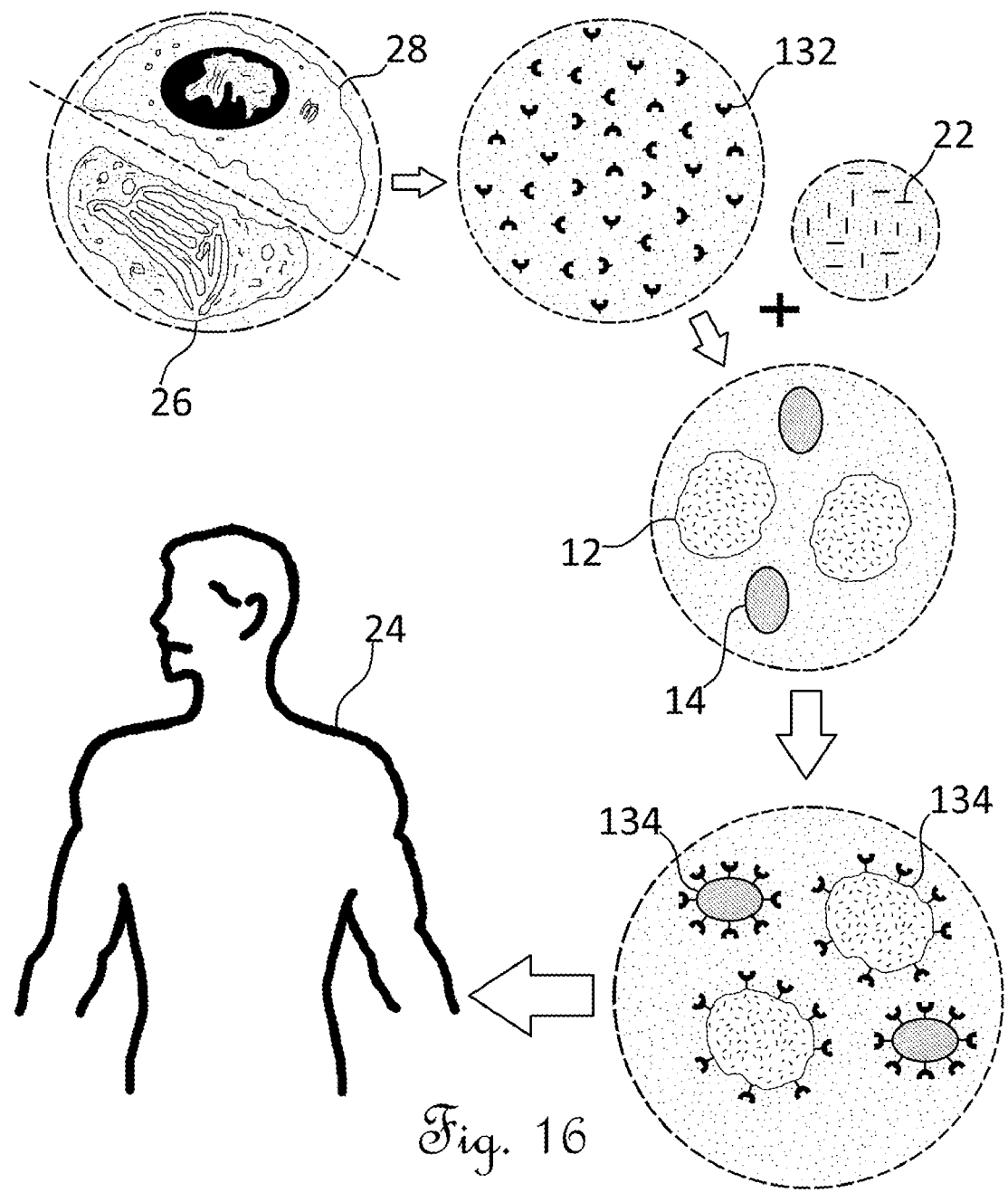
FIG. 16 is a schematic description of the method of preparation of multivalent IL-4Rα biologic constructs (MBCs-IL4Rα).
Figure 17:
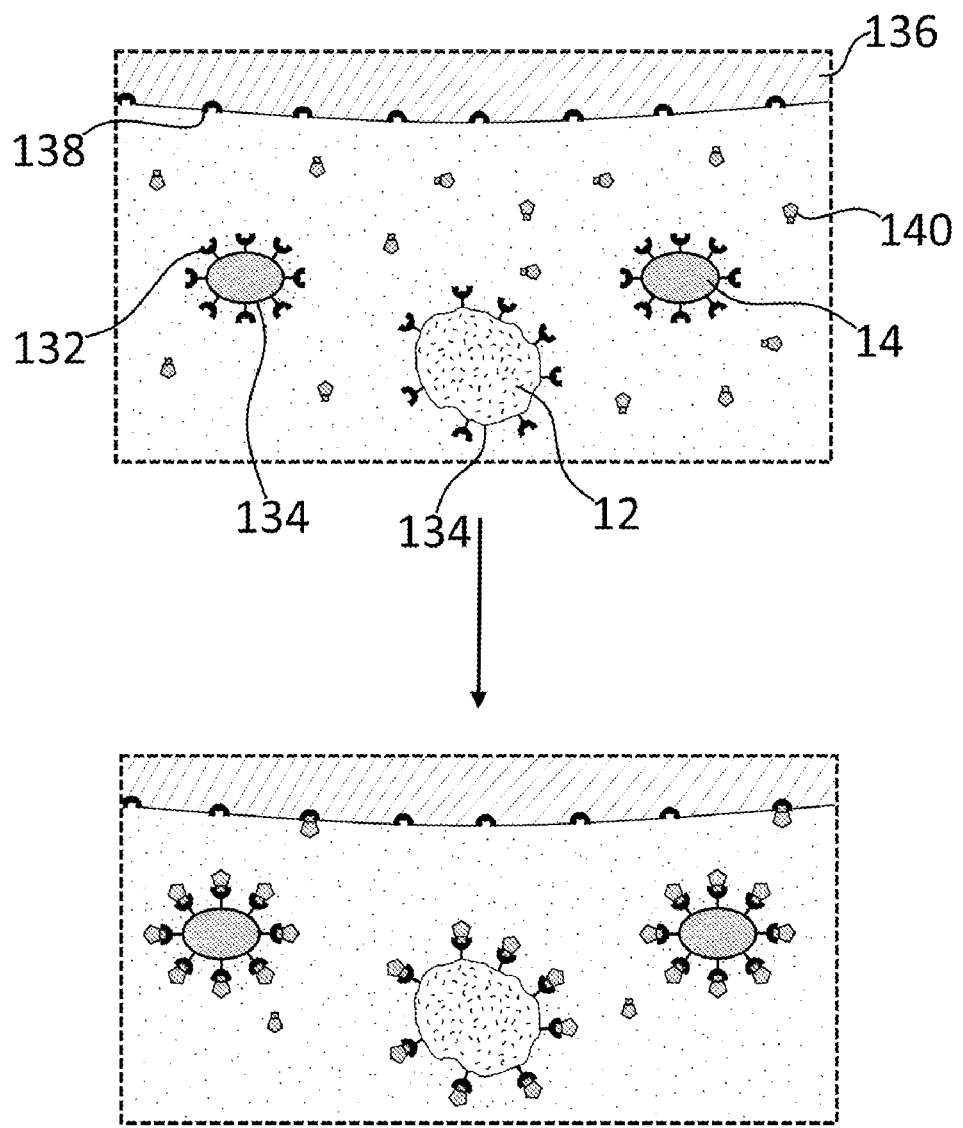
FIG. 17 is a schematic description of the interaction between multivalent IL-4Rα biologic constructs (MBCs-IL4Rα) and IL-4 molecules.

FIG. 16 and FIG. 17 are schematic descriptions showing the method of preparation and mechanism of action of multivalent interleukin-4 receptor a biologic constructs 134, hereinafter called MBCs-IL4Rα 134. The figures describe an example of the application of the proposed multivalent biologic constructs as consumptive inhibitors for a target cell receptor. FIG. 16 shows a schematic description of the method of preparation of MBCs-IL4Rα 134. Soluble IL-4Rα proteins 132, prepared by recombinant technology using bacterial 26 or eukaryotic 28 cells, are tethered via spacers 22 to a scaffold of micro-/nano-scale granules 14 and/or a scaffold of micro-/nano-scale corpuscles 12 to form MBCs-IL4Rα 134. Said MBCs-IL4Rα 134 can be given via a suitable route of administration to a recipient 24 to induce a therapeutic action in the form of consumptive inhibition of Interleukin-4 molecules.

FIG. 17 describes the mechanism of said MBCs-IL4Rα 134. The figure is a schematic description of a consumptive interaction between MBCs-IL4Rα 134 and native IL-4 molecules 140. In the upper portion of the figure; a part of IL-4 target cell 136 presents IL-4 receptors 138, while MBCs-IL4Rα 134 present multiple IL-4Rα molecules 132 tethered to a scaffold of micro-/nano-scale granules 14 and/or a scaffold of micro-/nano-scale corpuscles 12. MBCs-IL4Rα 134 compete with native IL-4 receptors 138 presented by IL-4 target cell 136 for said native IL-4 molecules 140. In the lower portion of the figure; each of said MBCs-IL4Rα 134 interacts simultaneously with multiple native IL-4 molecules 140, sparing IL-4 receptors 138 presented by said IL-4 target cell 136. This interaction consumes IL-4 molecules 140, preventing adequate amount from interacting with the corresponding IL-4 receptors 138. Consequently; the net result of the proposed consumptive inhibition, using multivalent decoy receptors in the form of multivalent IL-4Rα biologic constructs 134, is neutralization of native IL-4 molecules 140 leading to inefficient signaling.

Advantages: besides the basic advantages provided by the proposed structure of the multivalent biologic constructs; none of the prior art has proposed multivalent decoy receptors as consumptive inhibitors for IL-4 molecules. The proposed MBCs-IL4Rα have high avidity and long circulatory time. A potential therapeutic application is the treatment of moderate to severe atopic diseases.

Figure 18:
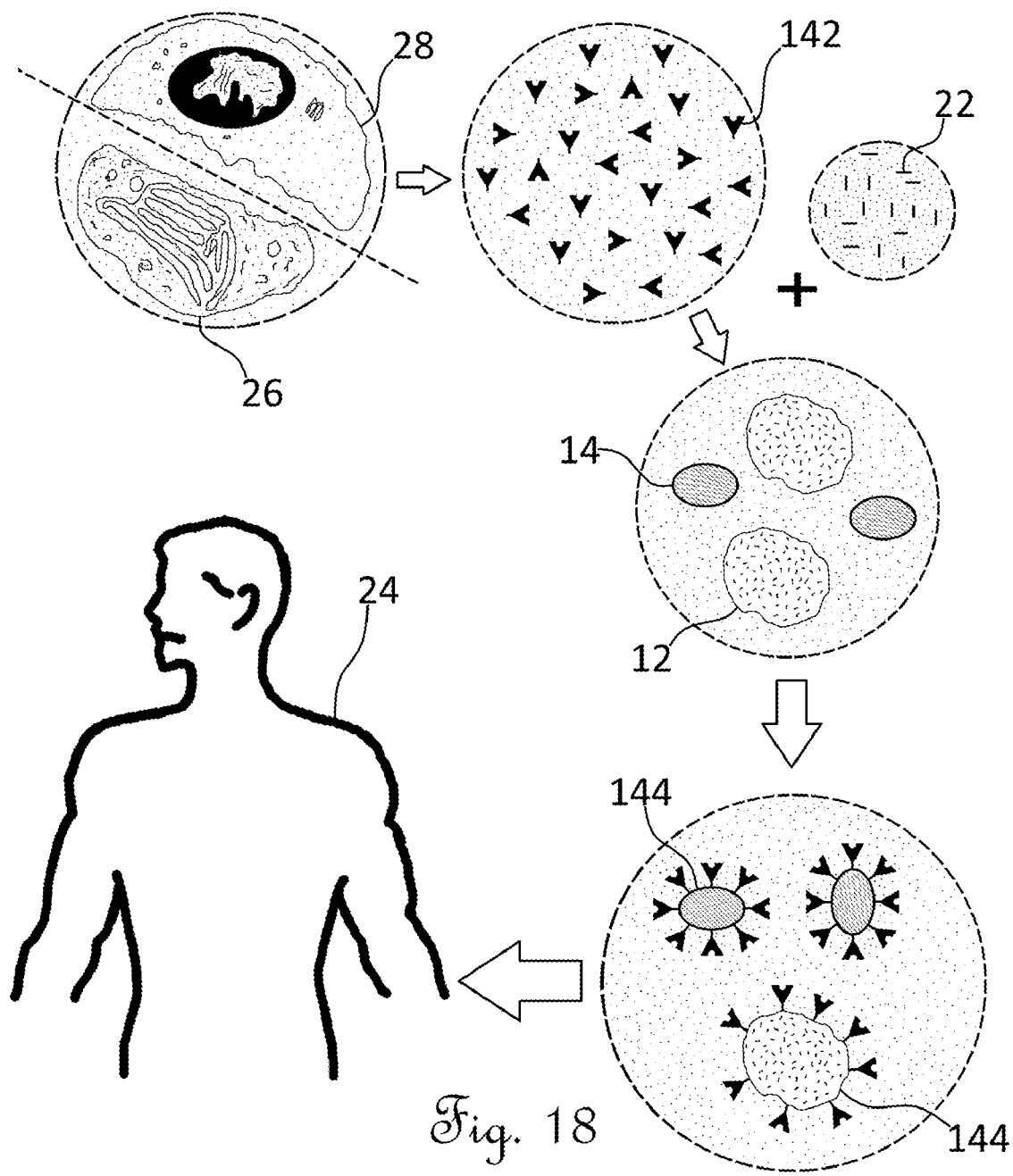
FIG. 18 is a schematic description of the method of preparation of multivalent IL-18BP biologic constructs (MBCs-IL18BP).
Figure 19:
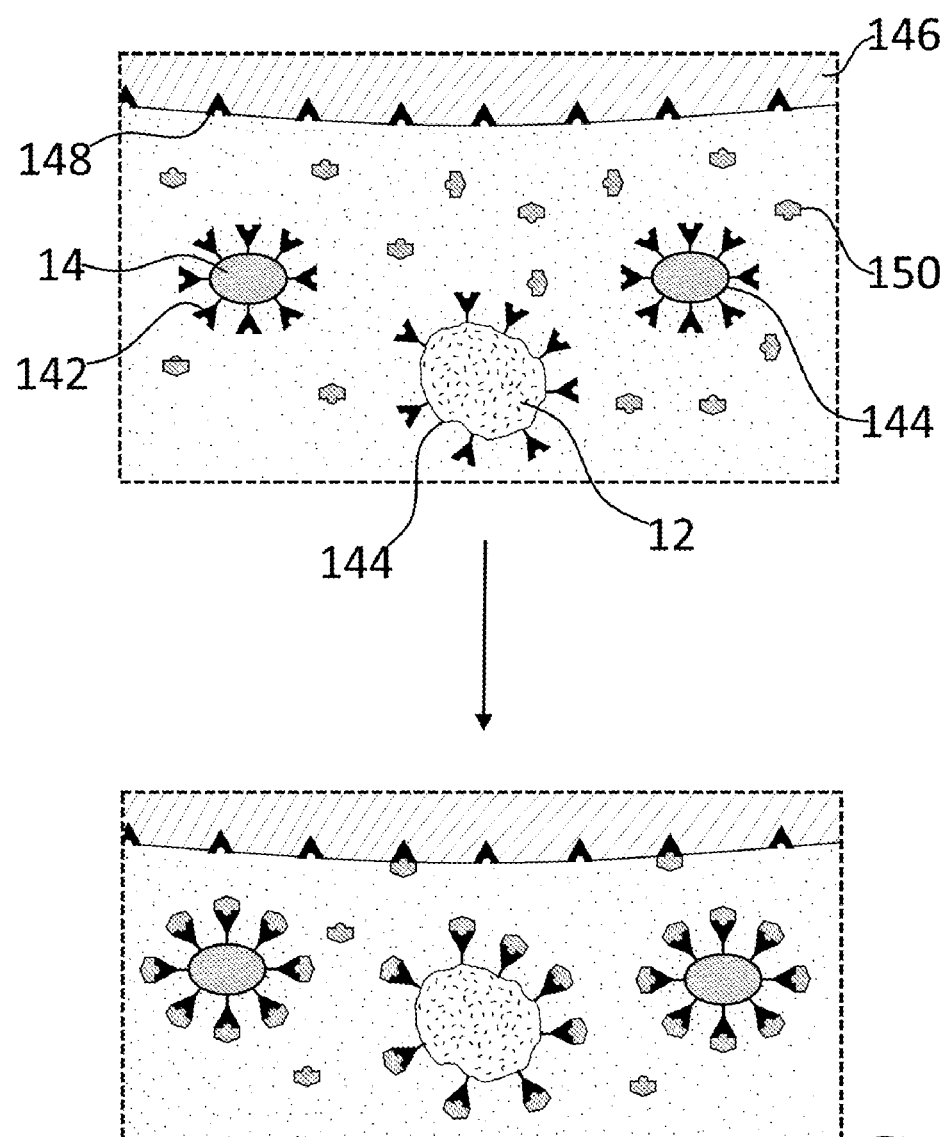
FIG. 19 is a schematic description of the interaction between multivalent IL-18BP biologic constructs (MBCs-IL18BP) and IL-18 molecules.

FIG. 18 and FIG. 19 are schematic descriptions showing the method of preparation and mechanism of action of multivalent Interleukin-18 binding protein biologic constructs 144, hereinafter called MBCs-IL18BP 144. The figures describe an example of the application of the proposed multivalent biologic constructs as consumptive inhibitors for a target cell receptor. FIG. 18 shows a schematic description of the method of preparation of MBCs-IL18BP 144. Soluble IL-18BP molecules 142, prepared by recombinant technology using bacterial 26 or eukaryotic 28 cells, are tethered via spacers 22 to a scaffold of micro-/nano-scale granules 14 and/or a scaffold of micro-/nano-scale corpuscles 12 to form MBCs-IL18BP 144. Said MBCs-IL18BP 144 can be given via a suitable route of administration to a recipient 24 to induce a therapeutic action in the form of consumptive inhibition of Interleukin-18 molecules.

FIG. 19 describes the mechanism of action of said MBCs-IL18BP 144. The figure is a schematic description of a consumptive interaction between MBCs-IL18BP 144 and native IL-18 molecules 150. In the upper portion of the figure; a part of IL-18 target cell 146 presents IL-18 receptors 148, while MBCs-IL18BP 144 present multiple IL-18BP molecules 142 tethered to a scaffold of micro-/nano-scale granules 14 and/or a scaffold of micro-/nano-scale corpuscles 12. MBCs-IL18BP 144 compete with native IL-18 receptors 148 presented by IL-18 target cell 146 for said native IL-18 molecules 150. In the lower portion of the figure; each of said MBCs-IL18BP 144 interacts simultaneously with multiple native IL-18 molecules 150, sparing IL-18 receptors 148 presented by said IL-18 target cell 146. This interaction consumes native IL-18 molecules 150, preventing adequate amount from interacting with the corresponding IL-18 receptors 148. Consequently; the net result of the proposed consumptive inhibition, using multivalent decoy receptors in the form of multivalent IL-18BP biologic constructs 144, is neutralization of native IL-18 molecules 150. Said consumptive inhibition hinders the proinflammatory action of IL-18 molecules 150 due to incompetent signaling leading to futile induction of interferon gamma.

Advantages: besides the basic advantages provided by the proposed structure of the multivalent biologic constructs; none of the prior art has proposed multivalent consumptive inhibitors for IL-18 molecules. The proposed multivalent IL-18BP biologic constructs have high avidity and long circulatory time. A potential therapeutic application is the treatment of moderate to severe multiple sclerosis.

Figure 20:
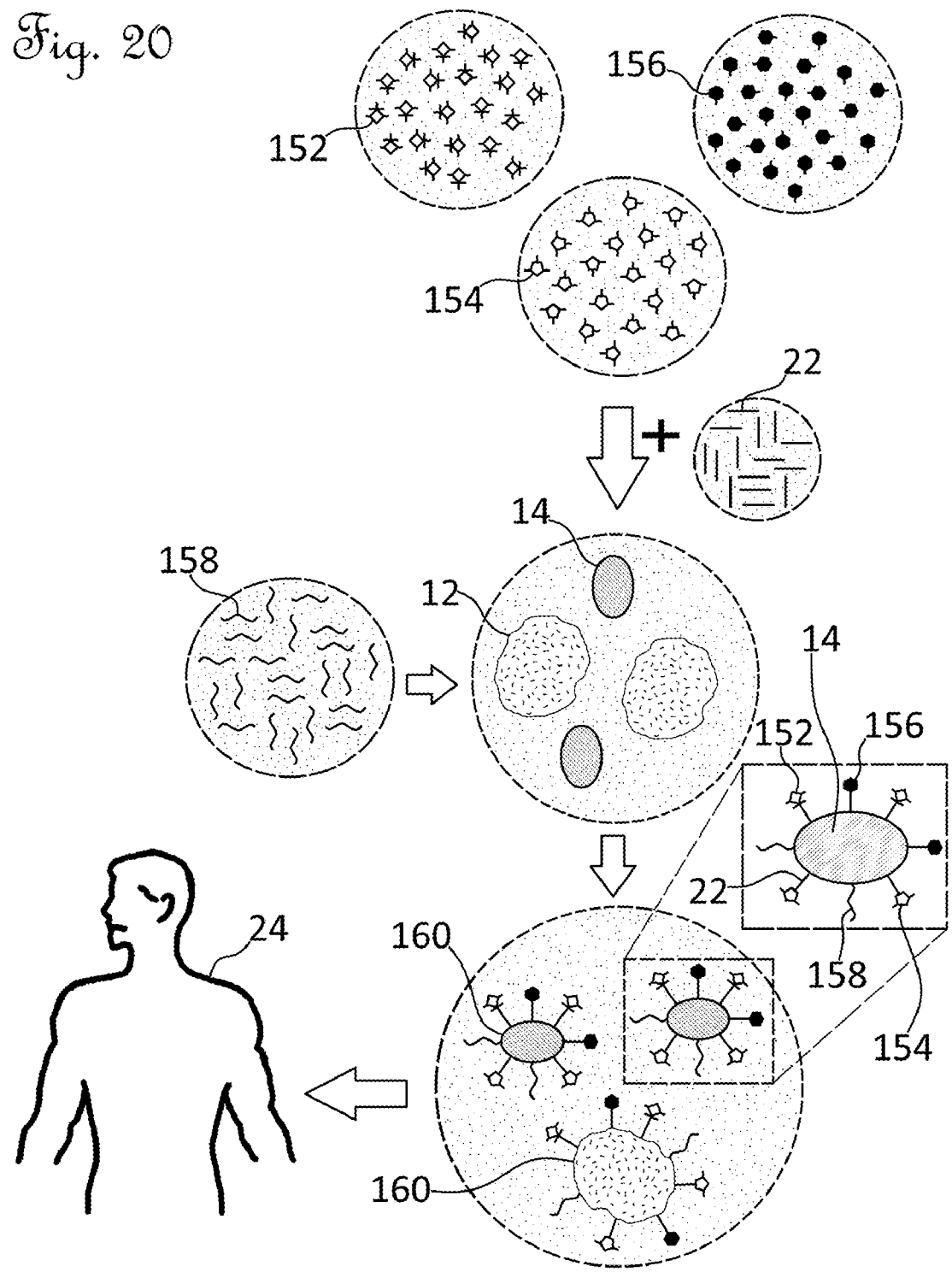
FIG. 20 is a schematic description of the method of preparation of multivalent HIV vaccine constructs (MVCs-HIV).
Figure 21A:
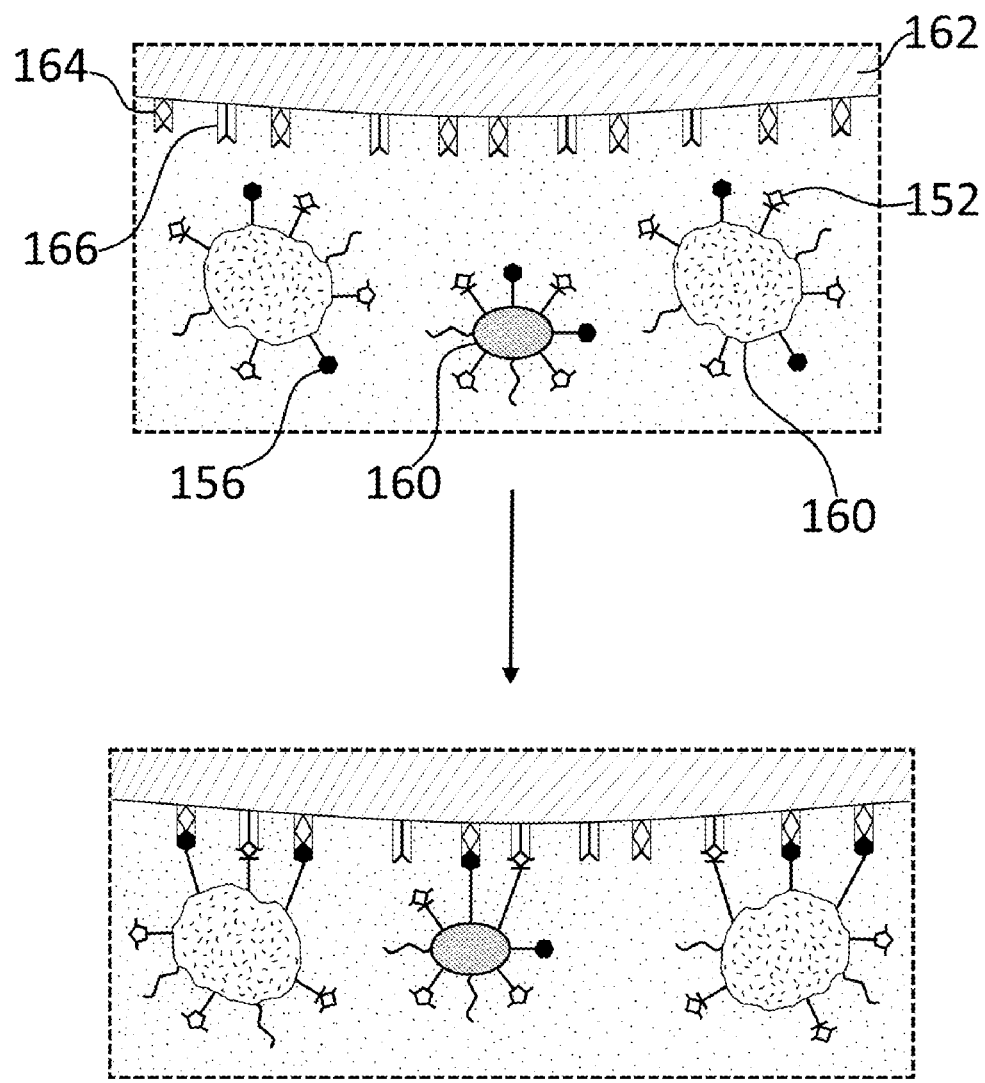
FIG. 21A is a schematic description of the interaction of multivalent HIV vaccine constructs (MVCs-HIV) with TLR 4 and TLR 2/1 of an antigen presenting cell (APC).
Figure 21B:
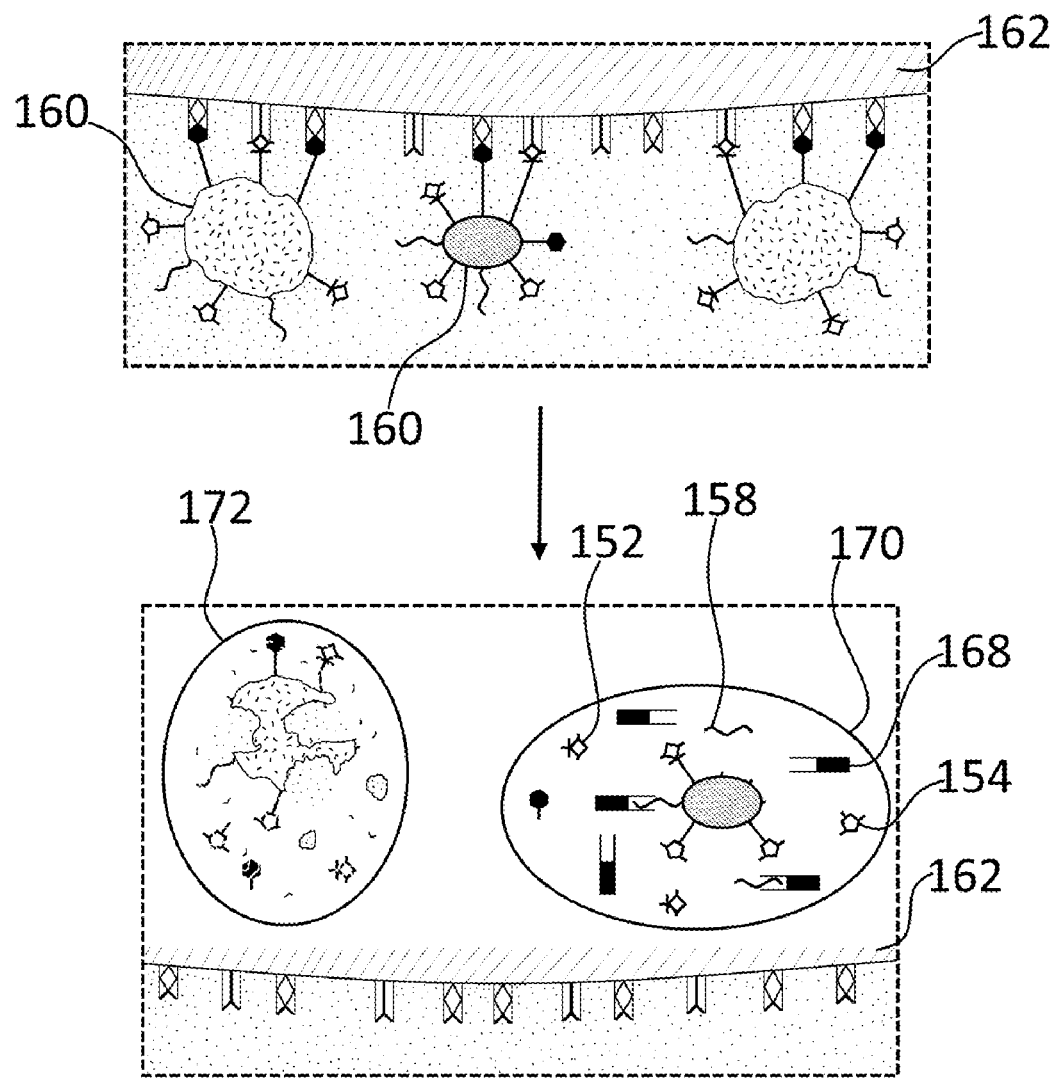
FIG. 21B is a schematic description of the interaction of multivalent HIV vaccine constructs (MVCs-HIV) with TLR 7 of an antigen presenting cell (APC).
Figure 22:
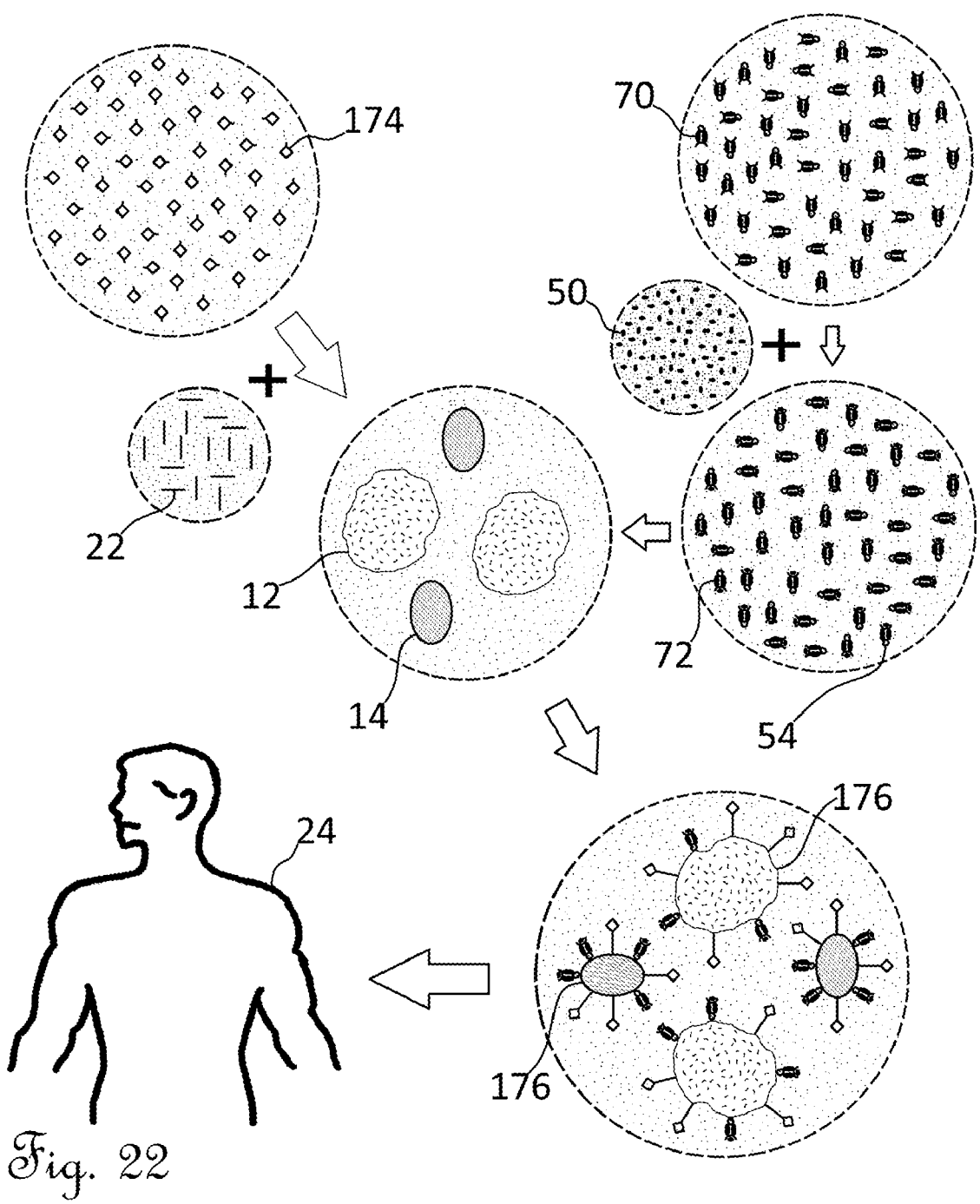
FIG. 22 is a schematic description of the method of preparation of multivalent B7-pMHC class II biologic constructs (MBCs-B7-pMHC class II).
Figure 23:
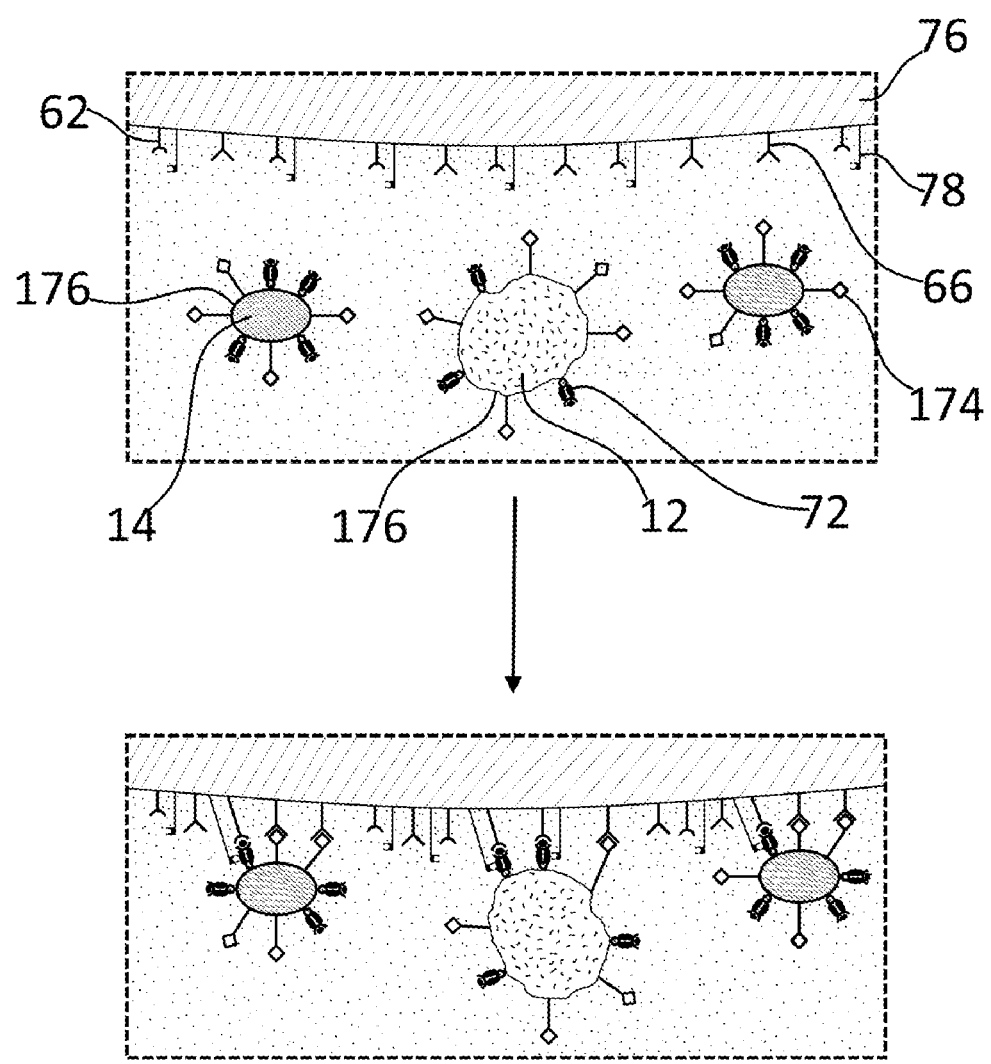
FIG. 23 is a schematic description of the interaction between T-helper cell and multivalent B7-pMHC class II biologic constructs (MBCs-B7-pMHC class II).
Figure 24:
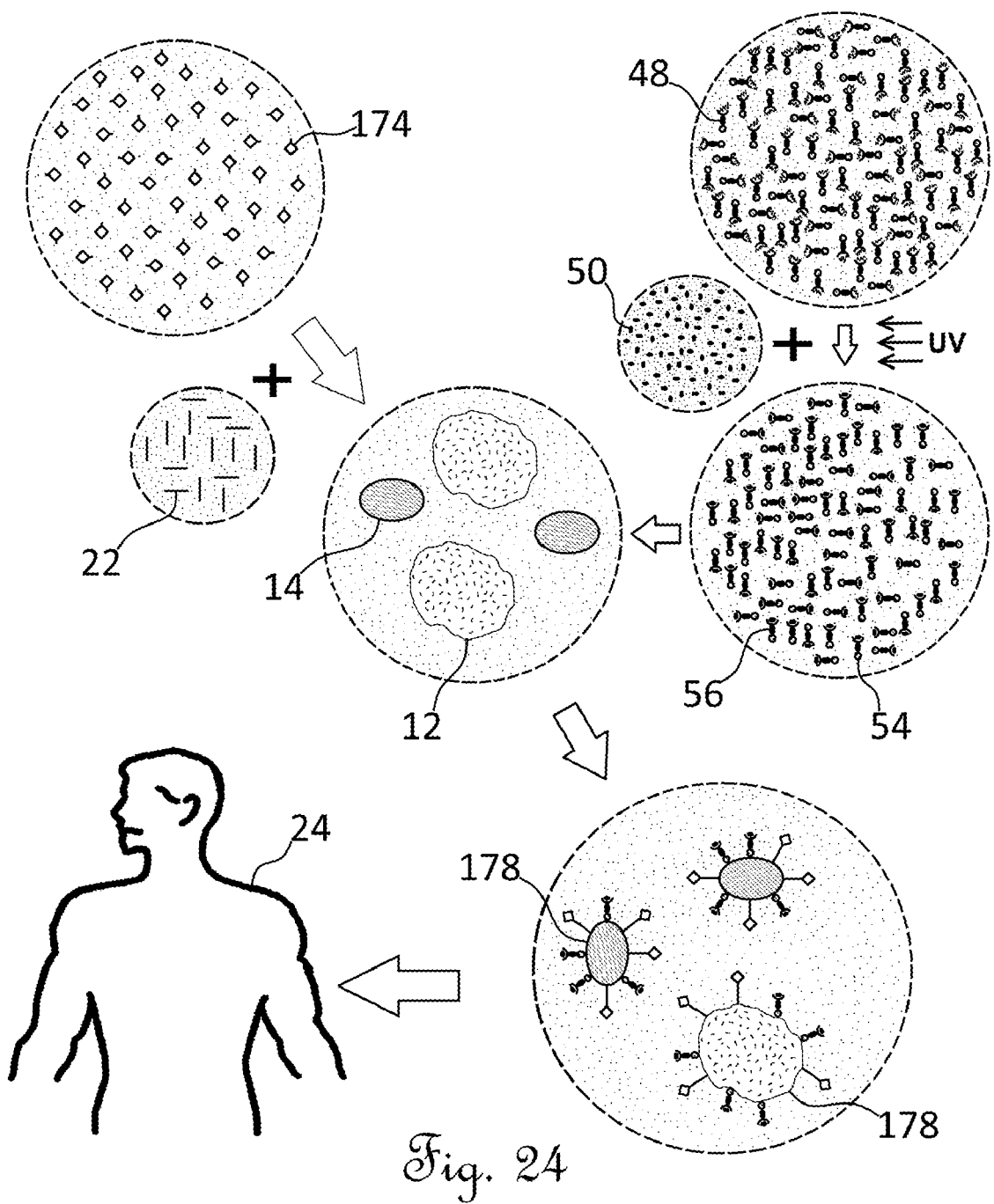
FIG. 24 is a schematic description of the method of preparation of multivalent B7-pMHC class I biologic constructs (MBCs-B7-pMHC class I).
Figure 25:
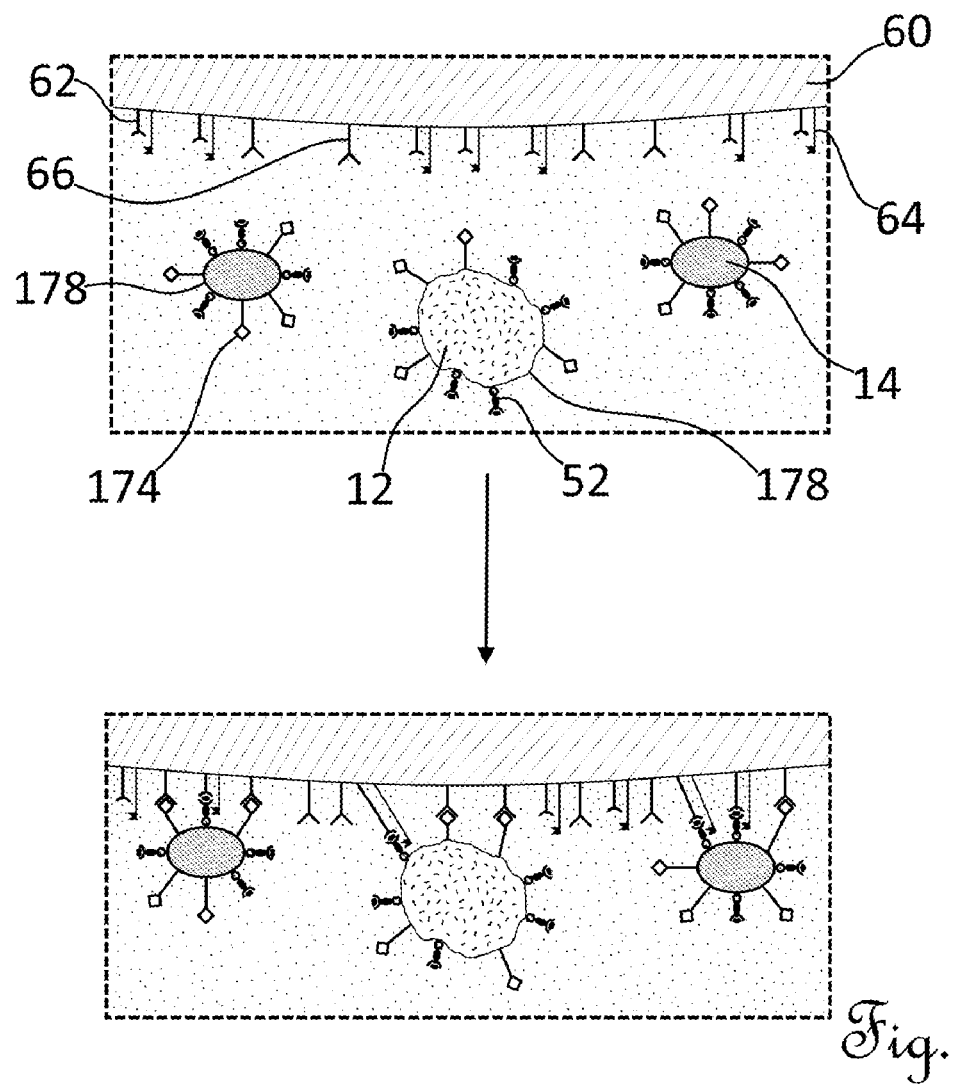
FIG. 25 is a schematic description of the interaction between T-cytotoxic cell and multivalent B7-pMHC class I biologic constructs (MBCs-B7-pMHC class I).
Figure 26:
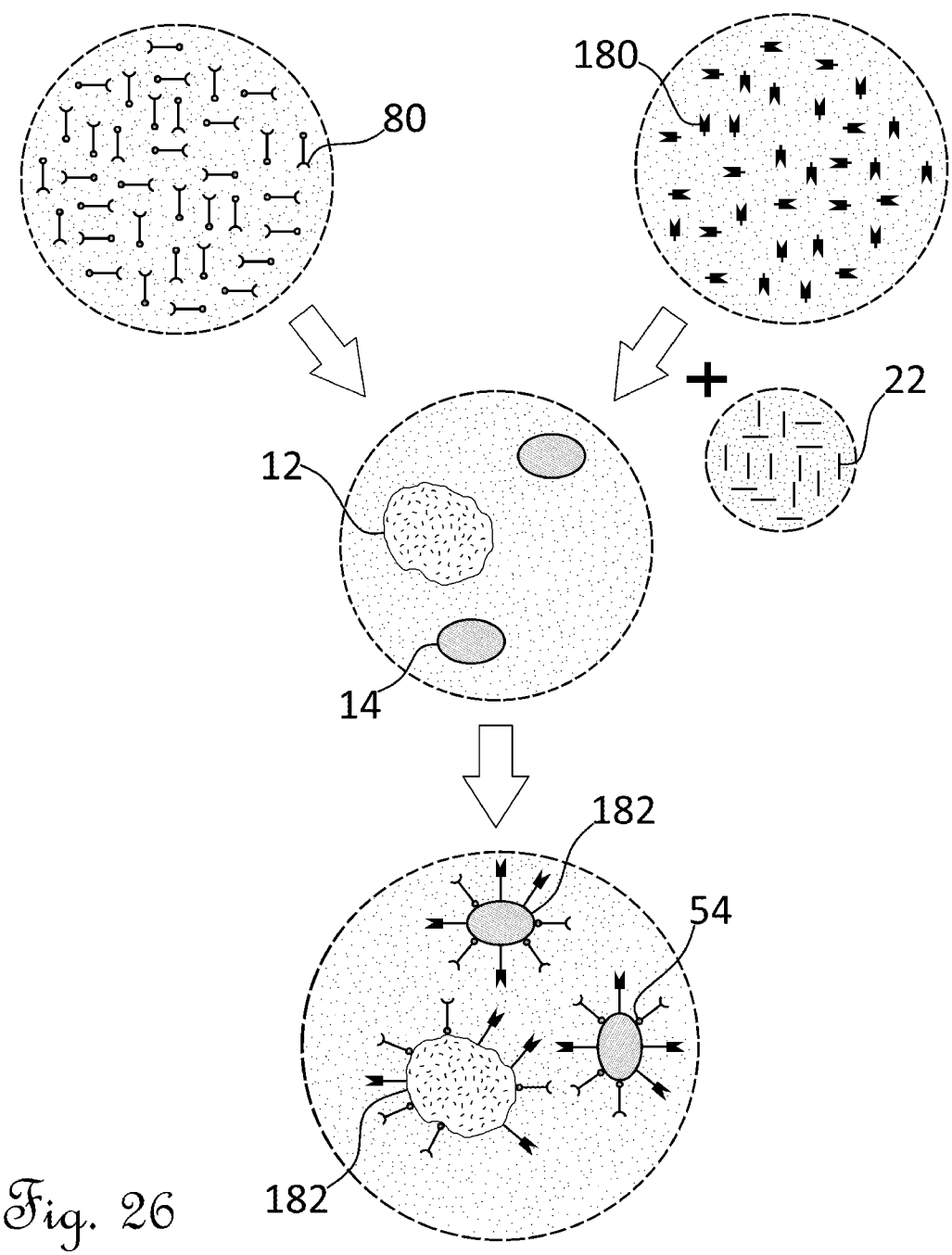
FIG. 26 is a schematic description of the method of preparation of multivalent TCRCD40L biologic constructs (MBCs-TCR-CD40L).
Figure 27:
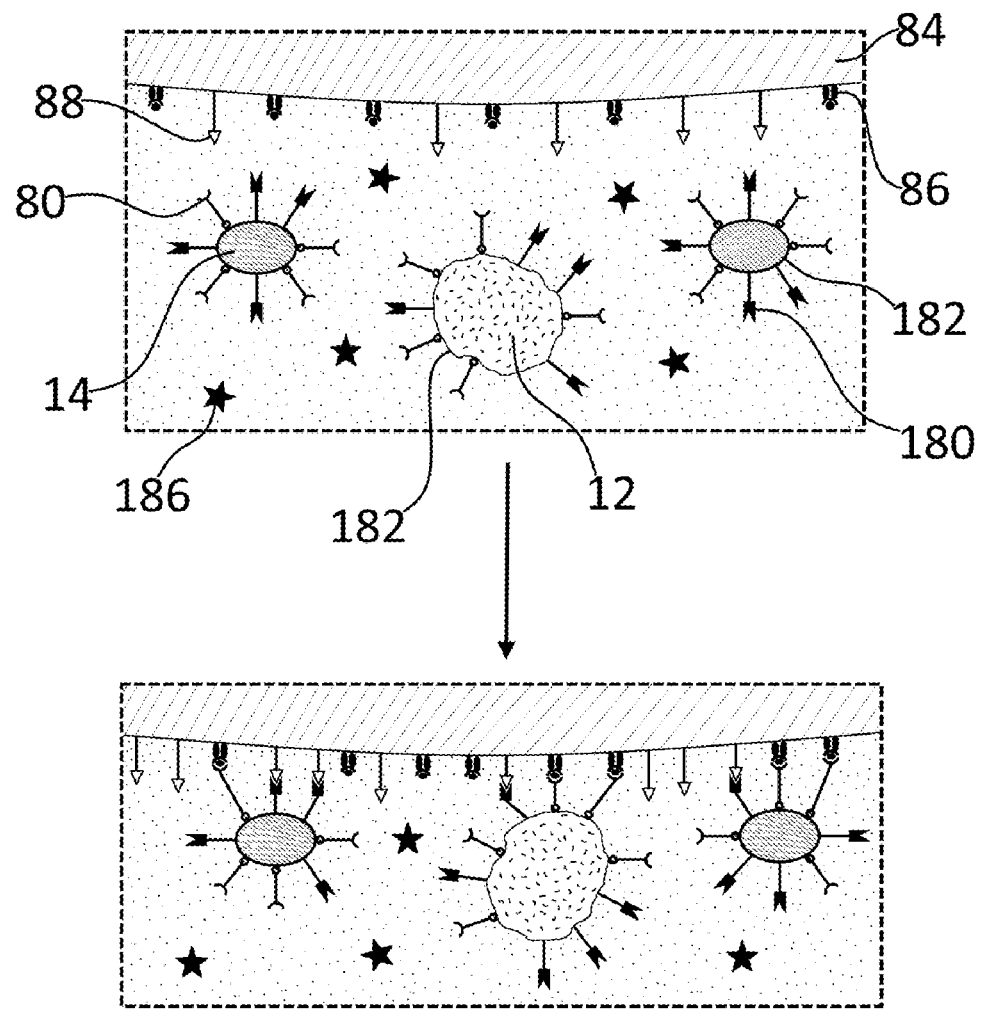
FIG. 27 is a schematic description of the interaction between follicular B cell and multivalent TCR-CD40L biologic constructs (MBCs-TCR-CD40L).

FIG. 20, FIG. 21A and FIG. 21B are schematic descriptions showing the method of preparation and mechanism of action of multivalent HIV vaccine constructs 160, hereinafter called MVCs-HIV 160. The figures describe an example of the application of the proposed multivalent biologic constructs as vaccines. FIG. 20 shows a schematic description of the structure and method of preparation of said MVCs-HIV 160. Each of MVCs-HIV 160 comprises a scaffold of micro-/nano-scale granules 14 and/or a scaffold of micro-/nano-scale corpuscles 12, into which two different protein subunits of HIV-1, herein in the preferred embodiment are the matrix protein P17 152 and tat 154, are tethered via spacers 22. Besides; the GU-rich LTRs 158 of the single-stranded viral RNA is also tethered to said scaffold 12, 14. Additionally; an immunogenic tail of lipid A 156 component of *E. Coli* lipopolysaccharide endotoxin is also tethered, via spacers 22, to said scaffold 12, 14. The matrix protein P17 152 is a structural protein critically involved in most stages of the life cycle of the retrovirus, and the second is the essential regulatory protein tat 154.

The preparation process of said MVCs-HIV 160 involves preparing of each bioactive component separately using conventional methods of production and purification. Two soluble HIV proteins, herein the essential regulatory protein tat 154 and the matrix protein P17 152, are prepared using recombinant technology. Besides; GU-rich LTRs 158 of the HIV-1 viral genome are restricted then amplified using the well-established enzymatic in vitro transcription (Nielsen; 2011). As well; conical lipid A molecules 156 are extracted from the *E. Coli* lipopolysaccharide endotoxin. Said bioactive components, tat 154, P17 152, LTRs 158 and lipid A molecules 156, are tethered to a scaffold of micro-/nano-scale granules 14 and/or a scaffold of micro-/nano-scale corpuscles 12 to form said MVCs-HIV 160. Spacers 22 are used to link tat 154, P17 152 and lipid A 156 to said scaffold 12, 14; while LTRs 158 are directly conjugated. Said MVCs-HIV 160 can be given via a suitable route of administration to a recipient 24 to provide active acquired immunity against a variety of HIV-1 strains.

FIG. 21A is a schematic description of the mechanism of action of said MVCs-HIV 160. The figure describes the interaction of MVCs-HIV 160 with TLR 4 164 and TLR 2/1 166 presented by an antigen presenting cell, mainly dendritic cell 162. Upon administration of MVCs-HIV 160; lipid A tail 156, which is a potent immunostimulator, is recognized by TLR4 164 presented by DCs 162. The TLR4 164 recognizes lipid A 156 in conjunction with MD2 and CD14 (not shown). Activation of TLR4 164 induces NF-κB activity, cytokine secretion and the maturation and trafficking of DCs 162 to draining lymph nodes. It further induces cytokine cascades of both Th1 and Th2 type responses with a preferential bias toward induction of a Th1 phenotype. Additionally; the functional heterodimer TLR2/1 166 recognizes the matrix protein P17 152 (Henrick et al; 2015). Activation of TLR2/1 166 augments NF-κB pathway, promotes leukocytic migration and induces early recruitment of leukocytes, mainly neutrophils, to the site of injection.

FIG. 21B is a schematic description of the mechanism of action of said MVCs-HIV 160. The figure describes the interaction of MVCs-HIV 160 with TLR7 168 of an antigen presenting cell, mainly dendritic cell 162. Upon internalization of MVCs-HIV 160; TLR7 168 recognizes GU-rich LTR 158 of the HIV single-stranded viral genome in the endosome 170. Activation of TLR7 168 triggers interferon pathway leading to the secretion of IFN α and β, as well as drives NF-κB-dependent inflammatory cytokine induction. Later; said MVCs-HIV 160 follow the lysosomal pathway; wherein the containing late endosome fuses with a lysosome (not shown) to form lysosome/late endosome hybrid 172, in which MVCs-HIV 160 are degraded by acid-dependent proteases. Polypeptides of tat 154 and P17 152 are further processed by proteasomes to form small peptides that are loaded on MHC class II (not shown) and presented on the cell surface of said DC 162.

Advantages: Over the prior art; the proposed MVCs-HIV is an advantageous candidate as an HIV vaccine. Each of MVCs-HIV, introduced to an APC, contains multiple subunits of HIV in addition to a highly immunogenic tail of lipid A. So the proposed MVCs-HIV provoke a more potent immune response via said tail of lipid A which activates TLR4, and also the LTR which activates TLR7. An aggressive immune response pledges proper processing and presentation of the remaining components of said MVCs-HIV, which are the protein subunits of tat and P17. The proper processing involves cytokines secretion, maturation and trafficking of DCs to draining lymph nodes. The rationality of providing said protein subunits tat and P17, is that the matrix protein P17 is readily recognized by TLR2/1, whereas the regulatory protein tat has a lesser mutation probability (Abbas; 2017). Other proteins, with low mutability, as the regulatory protein vpr (not shown) can replace tat on the MVCs-HIV. Although lipid A is toxic; but subcutaneous administration of appropriate doses and in the provided conjugated form limits its toxicity. MVCs-HIV seek to decrease the probability of acquiring the disease and/or control viremia during the acute and chronic stages of the disease.

FIG. 22 and FIG. 23 are schematic descriptions showing the method of preparation and mechanism of action of multivalent B7-pMHC class II biologic constructs 176, hereinafter called MBCs-B7-pMHC class II 176. Both figures describe an example of the application of the proposed multivalent biologic constructs to stimulate antigen-specific adaptive immunity. FIG. 22 describes the method of preparation of said MBCs-B7-pMHC class II 176. In vitro; recombinant peptide-free MHC class II molecules 70, which can be expressed in insect cells, are isolated and loaded with desirable antigenic peptides 50 to form pMHC class II complexes 72 (Sloan et al; 1995). Besides; recombinant B7 proteins 174, either B7.1 or B7.2 molecules, can be also expressed in bacterial or eukaryotic cells. Said pMHC class II complexes 72 and recombinant B7 proteins 174 are then conjugated to the proposed granular 14 and/or corpuscular 12 scaffolds, via linkers 54 and spacers 22 respectively. The resultant MBCs-B7-pMHC class II 176 can be given via a suitable route of administration to a recipient 24 to induce a therapeutic action in the form of stimulation of pluralities of T-helper (Th) cells against a specific antigen.

FIG. 23 describes the mechanism of action of said MBCs-B7-pMHC class II 176. The figure is a schematic description of the interaction between part of Th cell 76 and the MBCs-B7-pMHC class II 176. In the upper portion of the figure; Said part of Th cell 76 presents surface receptors, such as T cell receptors 62 (TCRs) along with CD4 markers 78 in addition to CD28 markers 66, while MBCs-B7-pMHC class II 176 present multiple pMHC class II 72 and multiple B7 ligands 174 tethered to a scaffold of micro-/nano-scale granules 14 and/or a scaffold of micro-/nano-scale corpuscles 12. In the lower portion of the figure; each of said MBCs-B7-pMHC class II 176 interacts simultaneously with multiple TCRs 62 along with CD4 markers 78 to give an antigen-specific main stimulatory signal 1, and multiple CD28 markers 66 to give an antigen-nonspecific costimulatory signal 2. These multiple interactions help stabilize the synapse between said Th cell 76 and MBCs-B7-pMHC class II 176, and initiate a sequel of intracellular reactions which leads to activation of the Th cell 76. The presented B7 proteins 174 of MBCs-B7-pMHC class II 176 can produce a costimulatory or a coinhibitory signal when paired to either CD28 markers 66 or CD152 markers (not shown) respectively. So said MBCs-B7-pMHC class II 176 exert a balanced modulation of Th cells 76 and limits the ability of progression of an excessive immune response.

FIG. 24 and FIG. 25 are schematic descriptions showing the method of preparation and mechanism of action of multivalent B7-pMHC class I biologic constructs 178, hereinafter called MBCs-B7-pMHC class I 178. Both figures describe an example of the application of the proposed multivalent biologic constructs to stimulate antigen-specific cell-mediated immunity. FIG. 24 describes the method of preparation of said MBCs-B7-pMHC class I 178. In vitro; a plurality of recombinant conditional pMHC class I molecules 48 are expressed in *E. coli* prokaryotes (Garboczi et al, 1992), then are loaded with desirable antigenic peptides 50, via peptide exchange protocols, to form pMHC class I complexes 56. Besides; recombinant B7 proteins 174, either B7.1 or B7.2 molecules, can be also expressed in bacterial or eukaryotic cells. Said pMHC class I complexes 56 and recombinant B7 proteins 174 are then conjugated to the proposed granular 14 and/or corpuscular 12 scaffolds, via linkers 54 and spacers 22 respectively. The resultant MBCs-B7-pMHC class I 178 can be given via a suitable route of administration to a recipient 24 to induce a therapeutic action in the form of stimulation of pluralities of T-cytotoxic (Tc) cells against a specific antigen.

FIG. 25 describes the mechanism of action of said MBCs-B7-pMHC class I 178. The figure is a schematic description of the interaction between part of Tc cell 60 and the MBCs-B7-pMHC class I 178. In the upper portion of the figure; Said part of Tc cell 60 presents surface receptors, such as T cell receptors 62 (TCRs) along with CD8 markers 64 in addition to CD28 markers 66, while MBCs-B7-pMHC class I 178 present multiple pMHC class I 52 and multiple B7 ligands 174 tethered to a scaffold of micro-/nano-scale granules 14 and/or a scaffold of micro-/nano-scale corpuscles 12. In the lower portion of the figure; each of said MBCs-B7-pMHC class I 178 interacts simultaneously with multiple TCRs 62 along with CD8 markers 64 to give an antigen-specific main stimulatory signal 1, and multiple CD28 markers 66 to give an antigen-nonspecific costimulatory signal 2. These multiple interactions help stabilize the synapse between said Tc cell 60 and MBCs-B7-pMHC class I 178, and initiate a sequel of intracellular reactions which leads to activation of said Tc cell 60.

FIG. 26 and FIG. 27 are schematic descriptions showing the method of preparation and mechanism of action of multivalent TCR-CD40 ligand biologic constructs 182, hereinafter called MBCs-TCR-CD40L 182. Both figures describe an example of the application of the proposed multivalent biologic constructs to stimulate T cell-dependent humoral immunity. FIG. 26 describes the method of preparation of said MBCs-TCR-CD40L 182. In vitro; pluralities of recombinant TCRs 80 are expressed in *E. coli* prokaryotes (Boulter et al; 2003). Besides; recombinant CD40L 180 can be also expressed in bacterial or eukaryotic cells. Said recombinant TCRs 80 and CD40L 180 are then conjugated to the proposed granular 14 and/or corpuscular 12 scaffolds, via linkers 54 and spacers 22 respectively. The resultant MBCs-TCR-CD40L 182 are used in vitro to expand antigen-specific follicular B cells (not shown) which-in turn-can be administered to a recipient 24.

FIG. 27 describes the mechanism of action of said MBCs-TCR-CD40L 182. The figure is a schematic description of the interaction between a part of follicular B cell 84 and the MBCs-TCR-CD40L 182. In the upper portion of the figure; Said part of follicular B cell 84 presents surface receptors, such as native pMHC class II proteins 86 in addition to CD40 markers 88, while MBCs-TCR-CD40L 182 present multiple TCRs 80 and multiple CD40 ligands 180 tethered to a scaffold of micro-/nano-scale granules 14 and/or a scaffold of micro-/nano-scale corpuscles 12. In the lower portion of the figure; each of said MBCs-TCR-CD40L 182 interacts simultaneously with multiple native pMHC class II proteins 86 to give a main stimulatory signal 1, and multiple CD40 markers 88 to give a costimulatory signal 2. These multiple interactions help stabilize the synapse between said follicular B cell 84 and MBCs-TCR-CD40L 182, and initiate a sequel of intracellular reactions which leads to activation of said follicular B cell 84 in the presence of specific cytokines as IL-21 186 within the in vitro medium. The use of MBCs-TCR-CD40L 182 in vivo is limited due to overlap interactions of recombinant TCRs 80 presented by said multimers 182 with native pMHC class II and native pMHC class I complexes presented by APCs (not shown) and nucleated cells (not shown) respectively, which competitively impedes the sequel of interactions needed to activate adaptive immunity.

Figure 28:
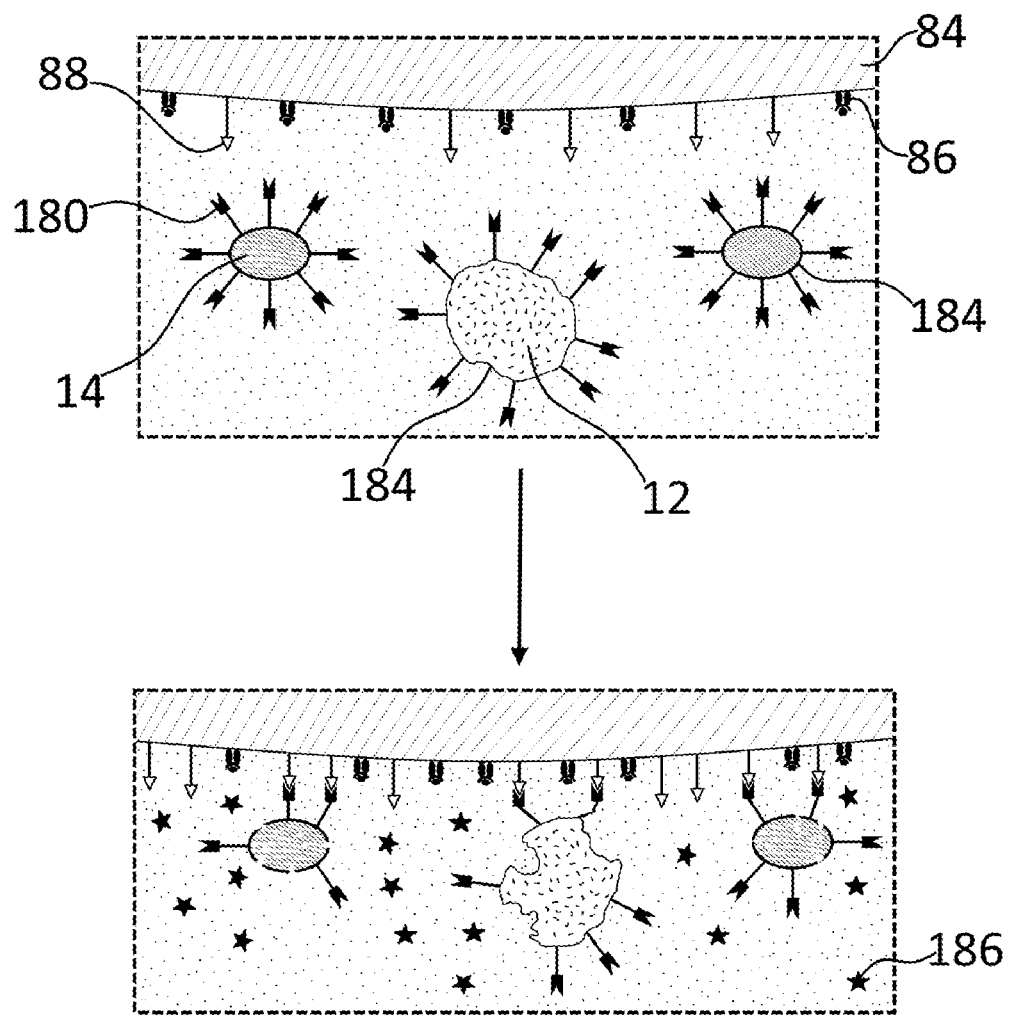
FIG. 28 is a schematic description of the interaction between follicular B cell and multivalent CD40L biologic constructs (MBCs-CD40L).

FIG. 28 is a schematic description of the interaction between monospecific MBCs-CD40L 184 with a part of follicular B cell 84. This is an alternative approach which can be used in vivo to aid the activation process of follicular B cells 84. In the upper portion of the figure; Said part of follicular B cell 84 presents surface receptors, such as native pMHC class II proteins 86 in addition to native CD40 markers 88, while MBCs-CD40L 184 present multiple CD40 ligands 180 tethered to a scaffold of micro-/nano-scale granules 14 and/or a scaffold of micro-/nano-scale corpuscles 12. In the lower portion of the figure; each of said MBCs-CD40L 184 interacts simultaneously with multiple native CD40 markers 88 to give a costimulatory signal 2. These multiple interactions help potentiate the synapse between said follicular B cell 84 and a Th cell (not shown), and augment the sequel of intracellular reactions which leads to activation of the follicular B cell 84 in the presence of specific cytokines as IL-21 186 released from the degraded scaffolds of MBCs-CD40L 184.

Drawings Reference Numbers

| No. | Reference | No. | Reference |
|---|---|---|---|
| 12 | Corpuscle (corpuscular scaffold) | 14 | Granule (granular scaffold) |
| 16 | X-Protein | 18 | Y-Protein |
| 20 | MBCs-X/Y | 22 | Spacer |
| 24 | Recipient | 26 | Prokaryote |
| 28 | Eukaryote | 30 | Target cell |
| 32 | X-protein receptor | 34 | Y-protein receptor |
| 36 | Polymeric core (PLGA) | 38 | Coat (PEG) |
| 40 | Liquid core | 42 | Pliable membrane (PLGA) |
| 44 | Underlay (PEG) | 46 | *E. Coli* cell |

Drawings Reference Numbers -continued

| No. | Reference | No. | Reference |
|---|---|---|---|
| 48 | Conditional peptide-MHC class I | 50 | Antigenic peptides |
| 52 | pMHC class I complex | 54 | Linker |
| 56 | Recombinant MHC class I molecule | 58 | MBCs-pMHC class I |
| 60 | Cytotoxic T cell (Tc) | 62 | Native T cell receptor (TCR) |
| 64 | CD8 marker | 66 | CD28 marker |
| 68 | Insect cell | 70 | Recombinant MHC class II molecules |
| 72 | pMHC class II complex | 74 | MBCs-pMHC class II |
| 76 | T-helper cell (Th) | 78 | CD4 marker |
| 80 | Recombinant TCR | 82 | MBCs-TCR |
| 84 | Follicular B cell | 86 | Native pMHC class II protein |
| 88 | CD40 marker | 90 | MBCs-antiCD20 mAb |
| 92 | Anti-CD20 mAb | 94 | Hybridoma cell |
| 96 | HAT medium | 98 | Resistant B cell |
| 100 | CD20 antigen | 102 | Human neonatal kidney cell |
| 104 | Urokinase molecule | 106 | Biotinylated urokinase |
| 108 | Biotin | 110 | Streptavidin |
| 112 | MBCs-UK | 114 | Activated platelet |
| 116 | Fibrin | 118 | Plasminogen |
| 120 | Plasmin | 122 | IL-1Ra molecule |
| 124 | MBCs-IL1Ra | 126 | IL-1 target cell |
| 128 | IL-1 receptor | 130 | Native IL-1 molecule |
| 132 | IL-4Rα molecules | 134 | MBCs- IL4Rα |
| 136 | IL-4 target cell | 138 | IL-4 receptor |
| 140 | Native IL-4 molecule | 142 | IL-18BP molecules |
| 144 | MBCs- IL18BP | 146 | IL-18 target cell |
| 148 | IL-18 receptor | 150 | Native IL-18 molecule |
| 152 | P17 protein | 154 | Tat protein |
| 156 | Lipid A | 158 | GU-rich LTR |
| 160 | MVCs- HIV | 162 | Dendritic cell (DC) |
| 164 | TLR4 | 166 | TLR2/1 |
| 168 | TLR7 | 170 | Endosome |
| 172 | Lysosome/late endosome hybrid | 174 | Recombinant B7 protein |
| 176 | MBCs- B7-pMHC class II | 178 | MBCs- B7-pMHC class I |
| 180 | CD40 ligands | 182 | MBCs-TCR-CD40L |
| 184 | MBCs-CD40L | 186 | IL-21 |

ABBREVIATIONS

| | |
|---|---|
| MBC(s) | Multivalent biologic construct(s) |
| MBCs-X/Y | Multivalent X/Y-protein biologic constructs |
| PEG | Polyethylene glycol |
| PLGA | Poly(lactic-co-glycolic acid) |
| RES | Reticuloendothelial system |
| MHC | Major histocompatibility complex |
| pMHC | Peptide-Major histocompatibility complex |
| MBCs-pMHC class I | Multivalent pMHC class I biologic constructs |
| UV | Ultraviolet rays |
| Tc | Cytotoxic T cell |
| TCR | T cell receptor |
| CD | Cluster of differentiation |
| MBCs-pMHC class II | Multivalent pMHC class II biologic constructs |
| Th | T-helper cell |
| IL | Interleukin |
| MBCs-TCR | Multivalent TCR biologic constructs |
| mAb | Monoclonal Antibody |
| MBCs-antiCD20 mAb | Multivalent anti-CD20 monoclonal antibodies biologic constructs |
| HAT medium | Hypoxanthine-Aminopterin-Thymidine medium |
| MBCs-UK | Multivalent urokinase biologic constructs |
| IL-1Ra | Interleukin 1 receptor antagonist |
| MBCs-IL1Ra | Multivalent interleukin 1 receptor antagonist biologic constructs |
| IL-4Rα | Interleukin-4 receptor α |
| MBCs-IL4Rα | Multivalent interleukin-4 receptor α biologic constructs |
| IL-18BP | Interleukin-18 binding protein |
| MBCs- IL18BP | Multivalent Interleukin-18 binding protein biologic constructs |
| MVCs- HIV | Multivalent HIV vaccine constructs |
| LTR | Long terminal repeat |

-continued

| ABBREVIATIONS | |
|---|---|
| TLR | Toll-like receptor |
| DCs | Dendritic Cells |
| MBCs- B7-pMHC class II | Multivalent B7-pMHC class II biologic constructs |
| MBCs- B7-pMHC class I | Multivalent B7-pMHC class I biologic constructs |
| MBCs-TCR-CD40L | Multivalent TCR-CD40 ligand biologic constructs |
| CD40L | CD40 ligand |
| APCs | Antigen presenting cells |
| MBCs-CD40L | Multivalent CD40 ligand biologic constructs |

| REFERENCES | |
|---|---|
| van der Weijden et al; 2014 | van der Weijden, Joep, Leonie E. Paulis, Martijn Verdoes, Jan CM van Hest, and Carl G. Figdor. "The right touch: design of artificial antigen-presenting cells to stimulate the immune system." Chemical Science 5, no. 9 (2014): 3355-3367. |
| knop et al; 2010 | Knop, Katrin, Richard Hoogenboom, Dagmar Fischer, and Ulrich S. Schubert. "Poly (ethylene glycol) in drug delivery: pros and cons as well as potential alternatives." Angewandte chemie international edition 49, no. 36 (2010): 6288-6308. |
| Garboczi et al, 1992 | Garboczi, David N., Deborah T. Hung, and Don C. Wiley. "HLA-A2-peptide complexes: refolding and crystallization of molecules expressed in *Escherichia coli* and complexed with single antigenic peptides." Proceedings of the National Academy of Sciences 89, no. 8 (1992): 3429-3433. |
| Rodenko et al, 2006 | Rodenko, Boris, Mireille Toebes, Sine Reker Hadrup, Wim JE Van Esch, Annemieke M. Molenaar, Ton NM Schumacher, and Huib Ovaa. "Generation of peptide-MHC class I complexes through UV-mediated ligand exchange." Nature protocols 1, no. 3 (2006): 1120. |
| Vollers and Stern; 2008 | Vollers, Sabrina S., and Lawrence J. Stern. "Class II major histocompatibility complex tetramer staining: progress, problems, and prospects." Immunology 123, no. 3 (2008): 305-313. |
| Stern and Wiley; 1992 | Stern, Lawrence J., and Don C. Wiley. "The human class II MHC protein HLA-DR1 assembles as empty $\alpha\beta$ heterodimers in the absence of antigenic peptide." Cell 68, no. 3 (1992): 465-477. |
| Sloan et al; 1995 | Sloan, Victor S., Patricia Cameron, Gene Porter, Maureen Gammon, Miguel Amaya, Elizabeth Mellins, and Dennis M. Zaller. "Mediation by HLA-DM of dissociation of peptides from HLA-DR." Nature 375, no. 6534 (1995): 802. |
| Boulter et al; 2003 | Boulter, Jonathan M., Meir Glick, Penio T. Todorov, Emma Baston, Malkit Sami, Pierre Rizkallah, and Bent K. Jakobsen. "Stable, soluble T-cell receptor molecules for crystallization and therapeutics." Protein engineering 16, no. 9 (2003): 707-711. |
| Tang et al; 1997 | Tang, Wei, Zi-Yong Sun, Ralph Pannell, Victor Gurewich, and Jian-Ning Liu. "An efficient system for production of recombinant urokinase-type plasminogen activator." Protein expression and purification 11, no. 3 (1997): 279-283. |
| Fairhead and Howarth; 2015 | Fairhead, Michael, and Mark Howarth. "Site-specific biotinylation of purified proteins using BirA." In Site-Specific Protein Labeling, pp. 171-184. Humana Press, New York, NY, 2015. |
| Alon et al; 1990 | Alon, Ronen, Edward A. Bayer, and Meir Wilchek. "Streptavidin contains an RYD sequence which mimics the RGD receptor domain of fibronectin." Biochemical and biophysical research communications 170, no. 3 (1990): 1236-1241. |
| Nielsen; 2011 | Nielson, Henrik. "RNA - Methods and Protocols." Humana Press, 2011. |
| Henrick et al; 2015 | Henrick, Bethany M., Xiao-Dan Yao, Kenneth Lee Rosenthal, and INFANT Study Team. "HIV-1 structural proteins serve as PAMPs for TLR2 heterodimers significantly increasing infection and innate immune activation." Frontiers in immunology 6 (2015): 426. |

-continued

| REFERENCES | |
|---|---|
| Abbas; 2017 | Abbas, Eslam. "Mathematical Analysis of the Probability of Spontaneous Mutations in HIV-1 Genome and Their Role in the Emergence of Resistance to Anti-Retroviral Therapy." arXiv preprint arXiv: 1705.06132 (2017). |

Conclusion

The proposed multivalent biologic constructs are designed as therapeutic agents to overcome cell resistance, to inhibit target binding sites, as vaccines, as thrombolytics, or as immunomodulators. They basically comprise bioactive biomolecules, mostly recombinant proteins or functional frictions of proteins prepared by recombinant technology, tethered to a scaffold of a specific structure.

While my above description contains many specificities, these should not be construed as limitations on the scope of the invention, but rather as an exemplification of preferred embodiments thereof. Many other variations are possible. Accordingly, the scope of the invention should be determined not by the embodiments illustrated, but by the appended claims and their legal equivalents.

I claim:

1. A multivalent biologic construct for inducing a therapeutic effect; comprising:

a scaffold of anisometric dimensions, comprising a biodegradable core coated with a hydrophilic coat of fluidic material, and a plurality of bioactive molecules tethered to said hydrophilic coat of fluidic material via spacers, wherein said plurality of bioactive molecules are presented to interact simultaneously with multiple corresponding binding sites.

2. The multivalent biologic construct according to claim 1; wherein the scaffold of anisometric dimensions can be a micro- or nano-granule, or a micro- or nano-corpuscle.

3. The micro- or nano-granule according to claim 2; comprises a non-spherical hydrophobic core of a biodegradable substance, surrounded by a hydrophilic coat of fluidic material.

4. The micro- or nano-corpuscle according to claim 2; comprises an internal biocompatible liquid core contained within a pliant biodegradable hydrophobic membrane surrounded by a hydrophilic coat of fluidic material; wherein amount of said internal biocompatible liquid core is adjusted to partially collapse said pliant membrane and said corpuscle can take an amoebic shape.

5. The micro- or nano-corpuscle according to claim 2; comprises an internal biocompatible liquid core contained within a pliant biodegradable hydrophobic membrane which sandwiched between two layers of a hydrophilic material; wherein amount of said internal biocompatible liquid core is adjusted to partially collapse said pliant membrane and said corpuscle can take an amoebic shape.

6. The multivalent biologic construct according to claim 1; wherein said plurality of bioactive molecules, tethered to said hydrophilic coat of fluidic material via spacers, can be identical resulting in a monospecific multivalent biologic construct, or different resulting in a polyspecific multivalent biologic construct.

7. A multivalent biologic construct for inducing thrombolysis; comprising:

a scaffold of streptavidin, and a plurality of biotinylated thrombolytic proteins tethered to said scaffold of streptavidin.

8. The multivalent biologic construct according to claim 7; wherein said biotinylated thrombolytic proteins are recombinant thrombolytic proteins linked to biotin molecules.

9. A multivalent vaccine construct against a virus; comprising:

a scaffold, antigenic recombinant viral proteins of said virus, wherein the antigenic recombinant viral proteins are tethered to said scaffold via spacers, a non-pathogenic segment of viral genome of said virus, wherein the non-pathogenic segment of viral genome is tethered to said scaffold, and an immunogenic biomolecule tethered to said scaffold.

* * * * *